United States Patent
De Castro Bizarro Duarte Canelas et al.

(10) Patent No.: US 11,142,783 B2
(45) Date of Patent: Oct. 12, 2021

(54) SEED TRAIN FOR LARGE SCALE ENZYME PRODUCTION

(71) Applicant: DSM IP Assets B.V., Heerlen (NL)

(72) Inventors: Andre De Castro Bizarro Duarte Canelas, Echt (NL); Wouter Adrianus Van Winden, Echt (NL)

(73) Assignee: DSM IP ASSETS B.V., Heerlen (NL)

( * ) Notice: Subject to any disclaimer, the term of this patent is extended or adjusted under 35 U.S.C. 154(b) by 225 days.

(21) Appl. No.: 16/305,333

(22) PCT Filed: Jun. 8, 2017

(86) PCT No.: PCT/EP2017/063975
§ 371 (c)(1),
(2) Date: Nov. 28, 2018

(87) PCT Pub. No.: WO2017/211957
PCT Pub. Date: Dec. 14, 2017

(65) Prior Publication Data
US 2020/0318149 A1   Oct. 8, 2020

(30) Foreign Application Priority Data
Jun. 9, 2016 (EP) .................................. 161736541

(51) Int. Cl.
*C12P 21/00* (2006.01)

(52) U.S. Cl.
CPC ........... *C12P 21/00* (2013.01); *C12P 2203/00* (2013.01)

(58) Field of Classification Search
None
See application file for complete search history.

(56) References Cited

PUBLICATIONS

International Search Report issued in counterpart Application No. PCT/EP2017/063975, dated Aug. 22, 2017.
D Humbird et al: Process Design and Economics for Biochemical Conversion of Lignocellulosic Biomass to Ethanol Dilute-Acid Pretreatment and Enzymatic Hydrolysis of Corn Stover, Technical Report NREL/TP-5100-47764, (May 1, 2011), pages I-IX,1-136.
Zsolt Barta et al: "Process Design and Economics of On-Site Cellulase Production on Various Carbon Sources in a Softwood-Based Ethanol Plant", Enzyme Research, vol. 84, No. 8, (Jan. 1, 2010), pp. 62-68.
Demetri Petrides et al: "Biopharmaceutical Process Optimization with Simulation and Scheduling Tools", Bio Engineering, vol. 1, No. 4, (Sep. 29, 2014), pp. 154-187.
Abdelaziz Toumi et al: "Design and Optimization of a Large Scale Biopharmaceutical Facility Using Process Simulation and Scheduling Tools" (Mar. 8, 2010), pp. 1-9.

*Primary Examiner* — Paul J Holland
(74) *Attorney, Agent, or Firm* — McBee, Moore & Vanik IP, LLC; Susan E. Shaw McBee; Chester G. Moore

(57) ABSTRACT

The invention relates to an optimized seed train expansion process.

18 Claims, No Drawings

US 11,142,783 B2

SEED TRAIN FOR LARGE SCALE ENZYME PRODUCTION

CROSS-REFERENCE TO RELATED APPLICATIONS

This application is a National Stage entry of International Application No. PCT/EP2017/063975, filed 8 Jun. 2017, which claims priority to European Patent Application No. 16173654.1, filed 9 Jun. 2016.

BACKGROUND

Field of the Invention

The invention relates to a process for producing a fermentation product, such as an enzyme or enzyme composition, comprising an optimized seed train process.

Description of Related Art

One of the main contributors to the overall costs of producing ethanol from biomass are the cellulolytic enzymes used in hydrolysis of the biomass. The cost of enzymes represents a significant part in the overall production costs and therefore improvement of cellulolytic microorganisms, enhancement of the hydrolytic capacity of cellulolytic enzymes, and optimization of the technology of enzyme production are essential today in order to further reduce the enzyme costs for the biomass-to-bioethanol process.

The on-site production of cellulolytic enzymes is an important strategy for the development of sustainable ethanol production processes from lignocellulosic biomass.

On-site production of cellulolytic enzymes encompasses a seed train process that is used to generate a sufficient amount of microbial biomass to inoculate large production bioreactors. A conventional seed train process begins with thawing of a cryopreserved cell bank vial, followed by multiple successive propagations into progressively larger culture vessels such as shake flasks, spinners, wave bags, and stirred bioreactors. When culture volume and cell density meet predetermined criteria, the culture is transferred to a production bioreactor in which cells continue to grow and divide and produce product.

This conventional seed train approach presents several challenges. Multiple manual manipulations are required during each step, which makes the whole seed train process vulnerable to contamination and operator error. In addition, conventional seed train processes are time-consuming due to the number of culturing steps, and due to the low cell numbers in the cryopreserved cell-bank vial. Moreover, large-scale production bioreactors are often started with low cell densities (e.g. less than $0.5 \times 10^6$ viable cells/ml). This is highly inefficient, as it requires a 5-10 day growth phase in order to reach production cell densities.

As the seed train can have a substantial impact on process performance in terms of productivity, profitability, and process control, there is a need to further improve seed train processes to further reduce the costs of producing ethanol from biomass.

SUMMARY

An object of the invention is to provide an improved production process for fermentation products such as polypeptides, e.g. enzymes. In particular, the object of the invention is to provide an improved production process for enzymes by fungi. Optimization and improvement lies in providing an improved seed train process.

DETAILED DESCRIPTION OF THE INVENTION

Throughout the present specification and the accompanying claims, the words "comprise" and "include" and variations such as "comprises", "comprising", "includes" and "including" are to be interpreted inclusively. That is, these words are intended to convey the possible inclusion of other elements or integers not specifically recited, where the context allows. The articles "a" and "an" are used herein to refer to one or to more than one (i.e. to one or at least one) of the grammatical object of the article. By way of example, "an element" may mean one element or more than one element.

An aspect of the present invention is a process for producing a fermentation product, the process comprising the steps of:
  a) preparing a fungal inoculum comprising fungal cells in an inoculum bioreactor,
  b) transferring the inoculum to a first of two or more production bioreactors, said first production bioreactor being ready for inoculation,
  c) culturing the fungal cells in the first production bioreactor to produce the fermentation product,
  d) emptying a second of the two or more production bioreactors, said second production bioreactor having reached the end of fermentation, and preparing the second production bioreactor for a new production fermentation,
  e) after step (b), but before completion of step (d), preparing a second fungal inoculum comprising fungal cells in the inoculum bioreactor,
  f) transferring the second inoculum to the second of the two or more production bioreactors, said second production bioreactor being ready for inoculation,
  g) culturing the fungal cells in the second production bioreactor to produce the fermentation product,
  h) emptying the first of the two or more production bioreactors, said first production bioreactor having reached the end of fermentation, and preparing the first production bioreactor for a new production fermentation,
  i) after step (f), but before completion of step (h), repeating at least steps (a)-(e).

An aspect of the present invention is also a process for producing a fermentation product, the process comprising the steps of:
  a) preparing a fungal inoculum comprising fungal cells in an inoculum bioreactor,
  b) transferring the inoculum to a first of three or more production bioreactors, said first production bioreactor being ready for inoculation,
  c) culturing the fungal cells in the first production bioreactor to produce the fermentation product,
  d) emptying a second of the three or more production bioreactors, said second production bioreactor having reached the end of fermentation, and preparing the second production bioreactor for a new production fermentation,
  e) after step (b), but before completion of step (d), preparing a second fungal inoculum comprising fungal cells in the inoculum bioreactor, f) transferring the second inoculum to the second of the three or more production bioreactors, said second production bioreactor being ready for inoculation, g) culturing the fungal cells in the second production bioreactor to produce the fermentation product, h) emptying a third of the three or more production bioreactors, said third production bioreactor having reached the end of fermentation, and preparing the third production bioreactor for a new production fermentation, i) after step (f), but before completion of step (h), preparing a third fungal inoculum comprising fungal cells in the inoculum bioreactor, j) transferring the third inoculum to the third of the three or more production bioreactors, said third production bioreactor being ready for inoculation, k) culturing the fungal cells in the third production bioreactor to produce the fermentation product, l) emptying the first of the three or more production bioreactors, said first production bioreactor having reached the end of fermentation, and preparing the first production bioreactor for a new production fermentation, m) after step (j), but before completion of step (l), repeating at least steps (a)-(e).

The above processes describe the constellation that a single inoculum bioreactor can be used to inoculate two or more production bioreactors or three or more production bioreactors. The present invention also encompasses processes wherein a single inoculum bioreactor can be used to inoculate four or more production bioreactors, five or more production bioreactors or even more than five or more production bioreactors. It is well within the reach of the skilled artisan to adapt the above processes to a constellation wherein an inoculum bioreactor is used to inoculate four or more production bioreactors, five or more production bioreactors or even more than five or more production bioreactors.

The present invention also encompasses processes wherein two or more inoculum bioreactors are used to inoculate two or more production bioreactors, three or more production bioreactors, four or more production bioreactors, five or more production bioreactors or even more than five or more production bioreactors. two or more inoculum bioreactors may have the same volume, but may also have a different volume. It is well within the reach of the skilled artisan to adapt the above processes to a constellation wherein two or more inoculum bioreactors are used to inoculate two or more production bioreactors, three or more production bioreactors, four or more production bioreactors, five or more production bioreactors or even more than five or more production bioreactors.

The generation of an adequate amount of microbial biomass for the inoculation of a production bioreactor is time- and cost-intensive. The seed train usually starts with one or more vials or ampoules comprising frozen or freeze-dried cells of a microorganism. The cells are then cultivated in several, i.e. two, three, four, five, six or even more cell expansion steps. In the cell expansion steps the amount of biomass is increased, while passaging into larger cultivation systems. Examples of cultivation systems that can be used are T-flasks, shake flasks, spinner flasks, roller bottles, wave bags, rolling tubes, spin tubes and bioreactors (e.g. stirred bioreactors). The volumes of these cultivation systems may vary from milliliters to cubic meters. The cultivation systems can be made from any suitable material, for example stainless steel.

In an embodiment the microorganism is a fungus. In an embodiment the fungus is a filamentous fungus, ergo, the fungal cells are filamentous fungal cells. In a preferred embodiment the fungus belongs to the genus *Rasamsonia* or *Aspergillus*, with *Rasamsonia emersonii* and *Aspergillus niger* being most preferred. "Filamentous fungi" include all filamentous forms of the subdivision Eumycota and Oomycota (as defined by Hawksworth et al., In, Ainsworth and Bisby's Dictionary of The Fungi, 8th edition, 1995, CAB International, University Press, Cambridge, UK). The filamentous fungi are characterized by a mycelial wall composed of chitin, cellulose, glucan, chitosan, mannan, and other complex polysaccharides. Vegetative growth is by hyphal elongation and carbon catabolism is obligatory aerobic. Filamentous fungal strains that can be used in the present invention include, but are not limited to, strains of *Acremonium, Agaricus, Aspergillus, Aureobasidium, Beauvaria, Cephalosporium, Ceriporiopsis, Chaetomium paecilomyces, Chrysosporium, Claviceps, Cochiobolus, Coprinus, Cryptococcus, Cyathus, Emericella, Endothia, Endothia mucor, Filibasidium, Fusarium, Geosmithia, Gilocladium, Humicola, Magnaporthe, Mucor, Myceliophthora, Myrothecium, Neocallimastix, Neurospora, Paecilomyces, Penicillium, Piromyces, Panerochaete, Pleurotus, Podospora, Pyricularia, Rasamsonia, Rhizomucor, Rhizopus, Scylatidium, Schizophyllum, Stagonospora, Talaromyces, Thermoascus, Thermomyces, Thielavia, Tolypocladium, Trametes, Trichoderma* and *Trichophyton*.

Several strains of filamentous fungi are readily accessible to the public in a number of culture collections, such as the American Type Culture Collection (ATCC), Deutsche Sammlung von Mikroorganismen and Zellkulturen GmbH (DSM), Centraalbureau Voor Schimmelcultures (CBS), and Agricultural Research Service Patent Culture Collection, Northern Regional Research Center (NRRL). Examples of such strains are known to the person skilled in the art.

In an embodiment the fungus is a recombinant fungus comprising one or more genes which can be homologous or heterologous to the fungus. "Heterologous" as used herein refers to a gene or polynucleotide that is not naturally occurring in the fungus. For example, a gene or polynucleotide of *Rasamsonia* when present in *Aspergillus* is considered to be heterologous. A gene or polynucleotide of *Rasamsonia emersonii* when present in *Rasamsonia byssochlamydoides* is also considered to be heterologous. A gene or polynucleotide of a specific *Rasamsonia emersonii* strain when present in another *Rasamsonia emersonii* strain is however considered to be homologous. When a synthetic gene or polynucleotide is introduced into a fungus, the synthetic gene or polynucleotide is also considered to be heterologous. In an embodiment, the fungus is a recombinant fungus comprising one or more genes which can be homologous or heterologous to the fungus, wherein the one or more genes encode enzymes that can degrade a cellulosic substrate. In an embodiment the fungus is a non-recombinant fungus comprising one or more genes which are homologous to the fungus. In an embodiment, the fungus is a non-recombinant fungus comprising one or more genes which are homologous to the fungus, wherein the one or more genes encode enzymes that can degrade a cellulosic substrate.

A seed train from a frozen vial to a production bioreactor comprises several steps. Frozen or freeze-dried cells are first inoculated in one or more first cultivation systems and cultured to prepare a first pre-culture. In an embodiment the first pre-culture is prepared in a batch mode. The first cultivation systems may have the same volume or a different volume. The gross vessel volume of the first cultivation systems may be from 5 ml to 10 l. In an embodiment the first cultivation systems may be T-flasks, shake flasks, spinner flasks, roller bottles, wave bags, rolling tubes, spin tubes and bioreactors. The cultivation medium, cultivation time, cultivation temperature and cultivation pH used in the preparation of the first pre-culture are dependent on among others the fungus to be cultured. The medium may comprise components such as for example one or more carbon sources, one or more nitrogen sources, a buffer, one or more minerals. The medium may be sterilized before use. In an embodiment the cultivation is done under agitation. In an embodiment the cultivation time may vary from 10 to 120 hours. In an embodiment the cultivation pH is from 3 to 7. In an embodiment the cultivation temperature is from 30° C. to 70° C.

In an embodiment the first pre-culture is transferred to a second cultivation system. The transfer can be done by any suitable means. If necessary, also two or more second cultivation systems can be inoculated with the first pre-culture. In an embodiment a second pre-culture is prepared in the second cultivation system(s). In an embodiment the preparation is done in a batch mode. The gross vessel volume of the second cultivation system may be from 50 l to 2,000 l. The cultivation medium, cultivation time, cultivation temperature and cultivation pH used in the preparation of the second pre-culture are dependent on among others the fungus to be cultured. The medium may comprise components such as for example one or more carbon sources, one or more nitrogen sources, a buffer, one or more minerals. The medium may be sterilized before use. In an embodiment the cultivation is done under aeration. In an embodiment the second cultivation system is stirred. In an embodiment the cultivation time may vary from 5 to 100 hours. In an embodiment the cultivation pH is from 3 to 7. In an embodiment the cultivation temperature is from 30° C. to 70° C.

In an embodiment the second pre-culture is transferred to an inoculum bioreactor. The transfer can be done by any suitable means. If necessary, also two or more inoculum bioreactors can be inoculated with the second pre-culture.

In an embodiment step (a) of the processes of the present invention comprises preparing a fungal inoculum comprising fungal cells in an inoculum bioreactor. In an embodiment the fungal inoculum comprising fungal cells is prepared in step (a) in a batch mode. The gross vessel volume of the inoculum bioreactor may be from 300 l to 15,000 l. The cultivation medium, cultivation time, cultivation temperature and cultivation pH used in the preparation of the fungal inoculum comprising fungal cells are dependent on among others the fungus to be cultured. The medium may comprise components such as for example one or more carbon sources, one or more nitrogen sources, a buffer, one or more minerals. The medium may be sterilized before use. In an embodiment the cultivation is done under aeration. In an embodiment the inoculum bioreactor is stirred. In an embodiment the cultivation time may vary from 1 to 60 hours. In an embodiment the cultivation pH is from 3 to 7. In an embodiment the cultivation temperature is from 30° C. to 70° C.

In an embodiment step (b) of the processes of the present invention comprises transferring the inoculum to a first of two or more production bioreactors, said first production bioreactor being ready for inoculation or transferring the inoculum to a first of three or more production bioreactors, said first production bioreactor being ready for inoculation. This means that there are at least two or at least three production bioreactors and the inoculum is transferred to one of them. The bioreactor to which the inoculum is transferred (the first bioreactor) is ready for inoculation. As used herein, "being ready for inoculation" means that the bioreactor has been emptied after a previous fermentation, cleaned, sterilized, and then filled with sterile medium or that the bioreactor has been emptied after a previous fermentation, cleaned, filled with medium, and then sterilized. The transfer can be done by any suitable means.

In an embodiment step (c) of the processes of the present invention comprises culturing the fungal cells in the first production bioreactor to produce the fermentation product. In an embodiment the fungal cells are cultured in the first production bioreactor in a fed-batch mode, a batch mode, a repeated batch mode, a repeated fed-batch mode or a continuous mode. Preferably, the fungal cells are cultured in a fed-batch mode. The step of culturing the fungal cells can be a batch phase at the start of the production process. In this step mainly fungal biomass is produced and optionally also an amount of the fermentation product of interest. The feed may start after a fixed time period or when certain criteria are met. Any suitable feed profile may be used. During the feed phase predominantly fermentation product is produced and to a lesser extent fungal biomass. The gross vessel volume of the first production bioreactor may be from 20,000 l to 300,000 l. The batch medium, the feed medium, cultivation time, cultivation temperature and cultivation pH used in the culturing of the fungal cells in the first production bioreactor are dependent on among others the fungus to be cultured. The media may comprise components such as for example one or more carbon sources, one or more nitrogen sources, a buffer, one or more minerals. The medium may be sterilized before use. In an embodiment the cultivation is done under aeration. In an embodiment the first production bioreactor is a bubble column bioreactor. In another embodiment the first production bioreactor is a stirred bioreactor. In an embodiment the cultivation time may vary from 10 to 300 hours. In an embodiment the cultivation pH is from 3 to 7. In an embodiment the cultivation temperature is from 30° C. to 70° C. During step (c) or at least a part thereof, the fermentation product is produced by the fungus.

In an embodiment step (d) of the processes of the present invention comprises emptying a second of the two or more production bioreactors or a second of the three or more production bioreactors, said second production bioreactor having reached the end of fermentation, and preparing the second production bioreactor for a new production fermentation. For a fed-batch fermentation, the end of fermentation is typically reached when the bioreactor is completely filled with (aerated) broth. At the end of the production fermentation, the bioreactor contains an amount of fermentation broth containing the final amount of produced product of interest. The broth is pumped out of the bioreactor to either a broth storage vessel or to a first downstream processing unit.

In an embodiment step (e) of the processes of the present invention comprises preparing a second fungal inoculum comprising fungal cells in the inoculum bioreactor. This preparation step is done after step (b), but before completion of step (d) of the processes of the present invention. In other words, the second fungal inoculum comprising fungal cells is prepared in the inoculum bioreactor at the same time as the fungal cells are cultured in the first production bioreactor to produce the fermentation product. "At the same time" as used herein does not mean that preparation of the second fungal inoculum comprising fungal cells needs to take as long as the complete culturing time of the fungal cells in the first production bioreactor, it may take only a part of the culturing time of the fungal cells in the first production bioreactor. For example, "at the same time" means that when the preparation of the second fungal inoculum comprising fungal cells in the inoculum bioreactor takes 20 hours and the culturing of the fungal cells in the first production bioreactor takes 100 hours, the preparation of the second fungal inoculum comprising fungal cells in the inoculum bioreactor should at least partly be performed within the 100 hours needed for culturing of the fungal cells in the first production bioreactor. To be able to prepare the second fungal inoculum comprising fungal cells in the inoculum bioreactor, a second pre-culture obtained as described above may be transferred to the inoculum bioreactor. In an embodiment the second fungal inoculum comprising fungal cells is prepared in a batch mode. The volume of the inoculum bioreactor has been described above. The cultivation medium, cultivation time, cultivation temperature and cultivation pH used in the preparation of the second fungal inoculum comprising fungal cells are dependent on among others the fungus to be cultured. The medium may comprise components such as for example one or more carbon sources, one or more nitrogen sources, a buffer, one or more minerals. The medium may be sterilized before use. In an embodiment the cultivation is done under aeration. In an embodiment the inoculum bioreactor is stirred. In an embodiment the cultivation time may vary from 1 to 60 hours. In an embodiment the cultivation pH is from 3 to 7. In an embodiment the cultivation temperature is from 30° C. to 70° C.

In an embodiment step (l of the processes of the present invention comprises transferring the second inoculum to the second of the two or more production bioreactors, said second production bioreactor being ready for inoculation, or transferring the second inoculum to the second of the three or more production bioreactors, said second production bioreactor being ready for inoculation. This means that there are at least two or at least three production bioreactors and the second inoculum is transferred to a production bioreactor different from the one to which the first inoculum was transferred. The term "being ready for inoculation" has been defined before. The transfer can be done by any suitable means.

In an embodiment step (g) of the processes of the present invention comprises culturing the fungal cells in the second production bioreactor to produce the fermentation product. In an embodiment the fermentation product produced in step (c) of the processes and the fermentation product produced in step (g) of the processes are the same. In another embodiment they differ. In an embodiment the fungal cells are cultured in the second production bioreactor in a fed-batch mode, a batch mode, a repeated batch mode, a repeated fed-batch mode or a continuous mode. Preferably, the fungal cells are cultured in a fed-batch mode. The step of culturing the fungal cells can be a batch phase at the start of the production process. In this step mainly fungal biomass is produced and optionally also an amount of the fermentation product of interest. The feed may start after a fixed time period or when certain criteria are met. Any suitable feed profile may be used. During the feed phase predominantly fermentation product is produced and to a lesser extent fungal biomass. The gross vessel volume of the second production bioreactor may be from 20,000 l to 300,000 l. In an embodiment the first and the second production bioreactor have an identical gross vessel volume. The batch medium, the feed medium, cultivation time, cultivation temperature and cultivation pH used in the culturing of the fungal cells in the second production bioreactor are dependent on among others the fungus to be cultured. The media may comprise components such as for example one or more carbon sources, one or more nitrogen sources, a buffer, one or more minerals. The medium may be sterilized before use. In an embodiment the cultivation is done under aeration. In an embodiment the second production bioreactor is a bubble column bioreactor. In another embodiment the production bioreactor is a stirred bioreactor. In an embodiment the cultivation time may vary from 10 to 300 hours. In an embodiment the cultivation pH is from 3 to 7. In an embodiment the cultivation temperature is from 30° C. to 70° C. During step (g) or at least a part thereof, the fermentation product is produced by the fungus.

In an embodiment step (h) of the processes of the present invention comprises emptying the first of the two or more production bioreactors, said first production bioreactor having reached the end of fermentation, and preparing the first production bioreactor for a new production fermentation. In another embodiment step (h) of the processes of the present invention comprises emptying a third of the three or more production bioreactors, said third production bioreactor having reached the end of fermentation, and preparing the third production bioreactor for a new production fermentation. For a fed-batch fermentation, the end of fermentation is typically reached when the bioreactor is completely filled with (aerated) broth. At the end of the production fermentation, the bioreactor contains an amount of fermentation broth containing the final amount of produced product of interest. The broth is pumped out of the bioreactor to either a broth storage vessel or to a first downstream processing unit.

In an embodiment step (i) of the processes of the present invention comprises repeating at least steps (a)-(e) after step (f), but before completion of step (h). In an embodiment after repeating steps (a)-(e), steps (f)-(i) of the processes of the present invention can be repeated. In an embodiment steps (a)-(i) of the processes of the present invention are done consecutively at least twice, at least three times, at least four times, at least five times, at least six times, at least seven times, at least eight times, at least nine times, at least ten times, or even more times.

In an embodiment step (i) of the processes of the present invention comprises preparing a third fungal inoculum comprising fungal cells in the inoculum bioreactor. This preparation step is done after step (f), but before completion of step (h) of the processes of the present invention. In other words, the third fungal inoculum comprising fungal cells is prepared in the inoculum bioreactor at the same time as the fungal cells are cultured in the second production bioreactor to produce the fermentation product. "At the same time" as used herein does not mean that preparation of the third fungal inoculum comprising fungal cells needs to take as long as the complete culturing time of the fungal cells in the second production bioreactor, it may take only a part of the culturing time of the fungal cells in the second production bioreactor. For example, "at the same time" means that when the preparation of the third fungal inoculum comprising fungal cells in the inoculum bioreactor takes 20 hours and the culturing of the fungal cells in the second production bioreactor takes 100 hours, the preparation of the third fungal inoculum comprising fungal cells in the inoculum bioreactor should at least partly be performed within the 100 hours needed for culturing of the fungal cells in the second production bioreactor. To be able to prepare the third fungal inoculum comprising fungal cells in the inoculum bioreactor, a second pre-culture obtained as described above may be transferred to the inoculum bioreactor. In an embodiment the third fungal inoculum comprising fungal cells is prepared in a batch mode. The volume of the inoculum bioreactor has been described above. The cultivation medium, cultivation time, cultivation temperature and cultivation pH used in the preparation of the third fungal inoculum comprising fungal cells are dependent on among others the fungus to be cultured. The medium may comprise components such as for example one or more carbon sources, one or more nitrogen sources, a buffer, one or more minerals. The medium may be sterilized before use. In an embodiment the cultivation is done under aeration. In an embodiment the inoculum bioreactor is stirred. In an embodiment the cultivation time may vary from 1 to 60 hours. In an embodiment the cultivation pH is from 3 to 7. In an embodiment the cultivation temperature is from 30° C. to 70° C.

In an embodiment step (j) of the processes of the present invention comprises transferring the third inoculum to the third of the three or more production bioreactors, said third production bioreactor being ready for inoculation. This means that there are at least three production bioreactors and the third inoculum is transferred to a production bioreactor different from the production bioreactors to which the first or second inoculum was transferred. The term "being ready for inoculation" has been defined before. The transfer can be done by any suitable means.

In an embodiment step (k) of the processes of the present invention comprises culturing the fungal cells in the third production bioreactor to produce the fermentation product. In an embodiment the fermentation product produced in step (c) of the processes and the fermentation product produced in step (g) of the processes and the fermentation product produced in step (k) of the processes are the same. In another embodiment they differ. In an embodiment the fungal cells are cultured in the third production bioreactor in a fed-batch mode, a batch mode, a repeated batch mode, a repeated fed-batch mode or a continuous mode. Preferably, the fungal cells are cultured in a fed-batch mode. The step of culturing the fungal cells can be a batch phase at the start of the production process. In this step mainly fungal biomass is produced and optionally also an amount of the fermentation product of interest. The feed may start after a fixed time period or when certain criteria are met. Any suitable feed profile may be used. During the feed phase predominantly fermentation product is produced and to a lesser extent fungal biomass. The gross vessel volume of the third production bioreactor may be from 20,000 l to 300,000 l. In an embodiment the first, second and/or third production bioreactor have an identical gross vessel volume. The batch medium, the feed medium, cultivation time, cultivation temperature and cultivation pH used in the culturing of the fungal cells in the third production bioreactor are dependent on among others the fungus to be cultured. The media may comprise components such as for example one or more carbon sources, one or more nitrogen sources, a buffer, one or more minerals. The medium may be sterilized before use. In an embodiment the cultivation is done under aeration. In an embodiment the second production bioreactor is a bubble column bioreactor. In another embodiment the second production bioreactor is a stirred bioreactor. In an embodiment the cultivation time may vary from 10 to 300 hours. In an embodiment the cultivation pH is from 3 to 7. In an embodiment the cultivation temperature is from 30° C. to 70° C. During step (k) or at least a part thereof, the fermentation product is produced by the fungus.

In an embodiment step (l) of the processes of the present invention comprises emptying the first of the three or more production bioreactors, said first production bioreactor having reached the end of fermentation, and preparing the first production bioreactor for a new production fermentation. In another embodiment step (l) of the processes of the present invention comprises emptying the second of the three or more production bioreactors, said second production bioreactor having reached the end of fermentation, and preparing the second production bioreactor for a new production fermentation. For a fed-batch fermentation, the end of fermentation is typically reached when the bioreactor is completely filled with (aerated) broth. At the end of the production fermentation, the bioreactor contains an amount of fermentation broth containing the final amount of produced product of interest. The broth is pumped out of the bioreactor to either a broth storage vessel or to a first downstream processing unit.

In an embodiment step (m) of the processes of the present invention comprises repeating at least steps (a)-(e) after step (j), but before completion of step (l). In an embodiment after repeating steps (a)-(e), steps (f)-(m) of the processes of the present invention can be repeated. In an embodiment steps (a)-(m) of the processes of the present invention are done consecutively at least twice, at least three times, at least four times, at least five times, at least six times, at least seven times, at least eight times, at least nine times, at least ten times, or even more times.

In an embodiment the ratio of the gross vessel volume of the inoculum bioreactor to the gross vessel volume of the first production bioreactor is from 1% to 15%, preferably from 2% to 8%, more preferably from 2% to 6%, even more preferably from 2% to 5% and most preferably from 2% to 4.5%, and/or the ratio of the gross vessel volume of the inoculum bioreactor to the gross vessel volume of the second production bioreactor is from 1% to 15%, preferably from 2% to 8%, more preferably from 2% to 6%, even more preferably from 2% to 5% and most preferably from 2% to 4.5%, and/or the ratio of the gross vessel volume of the inoculum bioreactor to the gross vessel volume of the third production bioreactor is from 1% to 15%, preferably from 2% to 8%, more preferably from 2% to 6% even more preferably from 2% to 5% and most preferably from 2% to 4.5%. The above ratios give the highest ratio of enzyme productivity over estimated CAPEX (capital expenditure) for a production facility. Lower ratios lead to lower CAPEX, but a longer batch phase of the production fermentation, which decreases productivity. Higher ratios lead to higher CAPEX, but a shorter batch phase of the production fermentation, which increases productivity.

In an embodiment the ratio of the gross vessel volume of the second cultivation system to the gross vessel volume of the inoculum bioreactor is from 0.5% to 20%, preferably from 1% to 10%, more preferably from 1% to 8% and even more preferably from 1% to 5%.

In an embodiment the ratio of the gross vessel volume of the first cultivation system to the gross vessel volume of the second cultivation system is from 0.1% to 20%, preferably from 0.5% to 10%, more preferably from 0.5% to 6% and even more preferably from 0.5% to 3%.

In an embodiment the fermentation product produced in the production bioreactor(s) can be any substance derived from fermentation. It includes, but is not limited to, an alcohol (such as arabinitol, butanol, ethanol, glycerol, methanol, 1,3-propanediol, sorbitol, and xylitol); an organic acid (such as acetic acid, acetonic acid, adipic acid, ascorbic acid, acrylic acid, citric acid, 2,5-diketo-D-gluconic acid, formic acid, fumaric acid, glucaric acid, gluconic acid, glucuronic acid, glutaric acid, 3-hydroxypropionic acid, itaconic acid, lactic acid, maleic acid, malic acid, malonic acid, oxalic acid, oxaloacetic acid, propionic acid, succinic acid, and xylonic acid); ketones (such as acetone); an amino acids (such as aspartic acid, glutamic acid, glycine, lysine, serine, tryptophan, and threonine); an alkane (such as pentane, hexane, heptane, octane, nonane, decane, undecane, and dodecane), a cycloalkane (such as cyclopentane, cyclohexane, cycloheptane, and cyclooctane), an alkene (such as pentene, hexene, heptene, and octene); a protein, a polypeptide, a vitamin, a pharmaceuticals, an animal feed supplement, a specialty chemical, a chemical feedstock, a plastic, a solvent, ethylene, an enzyme or enzyme composition. In a preferred embodiment the fermentation product produced in the production bioreactor(s) is an enzyme or an enzyme composition.

In an embodiment the fermentation product produced in the production bioreactor(s) is recovered. Recovery may take place during and/or after production. Processes for recovering fermentation products from a fungus, a culture medium or both are known to the skilled artisan and include, but are not limited to, biomass removal, centrifugation, (ultra)filtration and chromatography.

In another embodiment the fermentation product is not recovered and is part of a whole fermentation broth. A whole fermentation broth can be prepared by culturing non-recombinant and/or recombinant fungi. In an embodiment the fungus is a recombinant fungus comprising one or more genes which can be homologous or heterologous to the fungus. In an embodiment, the fungus is a recombinant fungus comprising one or more genes which can be homologous or heterologous to the fungus wherein the one or more genes encode enzymes that can degrade a cellulosic substrate.

Preferably, the fungal cells are killed in the whole fermentation broth. The whole fermentation broth may contain organic acid(s) (used for killing the cells), killed cells and/or cell debris, and culture medium.

The fermentation products may be prepared by fermentation of a suitable substrate with a suitable fungus, e.g. *Rasamsonia emersonii* or *Aspergillus niger*, wherein the fermentation products are produced by the fungus. The fungus may be altered to improve or to make the fermentation products. For example, the fungus may be mutated by classical strain improvement procedures or by recombinant DNA techniques. Therefore, the fungi mentioned herein can be used as such to produce the fermentation products or may be altered to increase the production or to produce altered fermentation products. In case the fermentation products are enzymes, the fungi may be altered to increase the production or to produce altered enzymes which might include heterologous enzymes, e.g. cellulases, thus enzymes that are not originally produced by that fungus. Preferably, a fungus, more preferably a filamentous fungus, is used to produce the fermentation products. The fermentation products produced by the fungus according to the processes of the present invention are preferably enzymes or enzyme compositions. Advantageously, a thermophilic or thermotolerant fungus is used.

Generally, the fungi are cultivated in a cell culture medium suitable for production of the fermentation product of interest. In a preferred embodiment the fermentation product is an enzyme or an enzyme composition. The enzyme or enzyme composition may be capable of degrading a cellulosic substrate. The enzyme or enzyme composition may be capable of hydrolyzing a cellulosic substrate. The cultivation takes place in a suitable nutrient medium comprising carbon and nitrogen sources and inorganic salts.

The whole fermentation broth can be prepared by growing the fungi to stationary phase and maintaining the fungi under limiting carbon conditions for a period of time sufficient to express the fermentation product. Once the fermentation product of interest is produced by the fungi, e.g. secreted into the fermentation medium, the whole fermentation broth can be used. The whole fermentation broth of the present invention may comprise fungi. In some embodiments, the whole fermentation broth comprises the unfractionated contents of the fermentation materials derived at the end of the fermentation. Typically, the whole fermentation broth comprises the spent culture medium and cell debris present after the fungi is grown to saturation, incubated under carbon-limiting conditions to allow production of the fermentation product or prevent oxygen limitation. In an embodiment, the whole fermentation broth comprises the spent cell culture medium, extracellular enzymes and fungi. In some embodiments, the fungi present in whole fermentation broth can be lysed, permeabilized, or killed using process known in the art to produce a cell-killed whole fermentation broth. In an embodiment, the whole fermentation broth is a cell-killed whole fermentation broth, wherein the whole fermentation broth containing the fungi cells are lysed or killed. In some embodiments, the cells are killed by lysing the fungi by chemical and/or pH treatment to generate the cell-killed whole broth of a fermentation of the fungi. In some embodiments, the cells are killed by lysing the fungi by chemical and/or pH treatment and adjusting the pH of the cell-killed fermentation mix to a suitable pH. In an embodiment, the whole fermentation broth comprises an organic acid and/or a salt thereof such as acetic acid, formic acid, propionic acid, benzoic acid, cyclohexanecarboxylic acid, 4-methylvaleric acid, phenylacetic acid, a salt of any of these organic acids, or any combination thereof.

The term "whole fermentation broth" as used herein refers to a preparation produced by cellular fermentation that undergoes no or minimal recovery and/or purification. For example, whole fermentation broths are produced when microbial cultures are grown to saturation, incubated under carbon-limiting conditions to allow protein synthesis (e.g., expression of enzymes by host cells) and secretion into cell culture medium. Typically, the whole fermentation broth is unfractionated and comprises spent cell culture medium, extracellular enzymes, and microbial, preferably non-viable, cells.

If needed, the whole fermentation broth can be fractionated and the one or more of the fractionated contents can be used. For instance, the killed cells and/or cell debris can be removed from a whole fermentation broth to provide a composition that is free of these components.

The whole fermentation broth may further comprise a preservative and/or anti-microbial agent. Such preservatives and/or agents are known in the art.

The whole fermentation broth as described herein is typically a liquid, but may contain insoluble components, such as killed cells, cell debris, culture media components, and/or insoluble enzyme(s). In some embodiments, insoluble components may be removed to provide a clarified whole fermentation broth.

In an embodiment the whole fermentation broth may be supplemented with one or more polypeptides. In an embodiment the whole fermentation broth may be supplemented with one or more enzyme activities that are not expressed endogenously, or expressed at relatively low level by the fungi, to improve the degradation of the cellulosic substrate, for example, to fermentable sugars such as glucose or xylose. The supplemental polypeptide(s) or enzyme(s) can be added as a supplement to the whole fermentation broth and the polypeptide(s) or enzyme(s) may be a component of a separate whole fermentation broth, or may be purified, or minimally recovered and/or purified.

In an embodiment the whole fermentation broth may be supplemented with at least another whole fermentation broth. The other whole fermentation broth may be derived from the same type of fungus or from another type of fungus, e.g. a first whole fermentation broth may be derived from *Rasamsonia*, while a second whole fermentation broth may be derived from *Rasamsonia* or *Aspergillus*.

In an embodiment the whole fermentation broth comprises a whole fermentation broth of a fermentation of a recombinant fungus overexpressing one or more enzymes. In an embodiment the whole fermentation broth comprises a whole fermentation broth of a fermentation of a recombinant fungus overexpressing one or more enzymes that can degrade a cellulosic substrate. Alternatively, the whole fermentation broth can comprise a mixture of a whole fermentation broth of a fermentation of a non-recombinant fungus and a whole fermentation broth of a fermentation of a recombinant fungus overexpressing one or more enzymes. Alternatively, the whole fermentation broth can comprise a mixture of a whole fermentation broth of a fermentation of a non-recombinant fungus and a whole fermentation broth of a fermentation of a recombinant fungus overexpressing one or more enzymes that can degrade a cellulosic substrate. In an embodiment, the whole fermentation broth comprises a whole fermentation broth of a fermentation of a fungus overexpressing a cellulase and/or a hemicellulase and/or a pectinase. Cellulases, hemicellulases and pectinases and other enzymes that can be overexpressed are described hereinafter. Alternatively, the whole fermentation broth can comprise a mixture of a whole fermentation broth of a fermentation of a non-recombinant fungus and a whole fermentation broth of a fermentation of a recombinant fungi overexpressing a cellulase and/or a hemicellulase and/or a pectinase. Alternatively, the whole fermentation broth can comprise a mixture of a whole fermentation broth of a fermentation of a recombinant fungus overexpressing one or more enzymes that degrade cellulosic substrate and a whole fermentation broth of a fermentation of a recombinant fungi overexpressing one or more other enzymes that degrade cellulosic substrate.

In an embodiment the process of the present invention further comprises the step of storing the fermentation products produced in step (c) and/or step (g) and/or step (k) in a storage tank. Storage in the storage tanks may be from 1 hour to 500 hours. Storage tanks may have a volume from 100,000 to 700,000 liters.

In an embodiment the enzyme or enzyme composition produced by the process of the present invention has cellulosic substrate degrading and/or carbohydrate hydrolysing activity. In other words, the enzyme or enzyme composition that is produced by the fungus has cellulosic substrate degrading and/or carbohydrate hydrolysing activity. The enzyme or enzyme composition may be derived from a fungus such as a filamentous fungus.

In an embodiment the fungus may produce two or more, for example, three, four, five, six, seven, eight, nine or even more enzymes. Some enzymes may be native, while others are heterologous. In an embodiment the fungus produces at least two cellulases. The at least two cellulases may contain the same or different activities.

In an embodiment the fungus may produce a lytic polysaccharide monooxygenase, an endoglucanase, a cellobiohydrolase and/or a beta-glucosidase.

The fungus may produce a cellulase and/or a hemicellulase and/or a pectinase from a source other than the fungus. In another embodiment after production by the fungus, the produced enzyme may be combined with one or more other enzymes. The combination of enzymes can then for instance be used in a process for degrading a cellulosic substrate as described herein and/or in a process for producing a fermentation product from a cellulosic substrate as described herein.

Enzymes produced by the fungus according to a process of the invention may comprise a beta-glucosidase (BG) from *Aspergillus*, such as *Aspergillus oryzae*, such as the one disclosed in WO 02/095014 or the fusion protein having beta-glucosidase activity disclosed in WO 2008/057637, or *Aspergillus fumigatus*, such as the one disclosed as SEQ ID NO:2 in WO 2005/047499 or SEQ ID NO:5 in WO 2014/130812 or an *Aspergillus fumigatus* beta-glucosidase variant, such as one disclosed in WO 2012/044915, such as one with the following substitutions: F100D, S283G, N456E, F512Y (using SEQ ID NO: 5 in WO 2014/130812 for numbering), or *Aspergillus aculeatus*, *Aspergillus niger* or *Aspergillus kawachi*. In another embodiment the beta-glucosidase produced is derived from *Penicillium*, such as *Penicillium brasilianum* disclosed as SEQ ID NO:2 in WO 2007/019442, or from *Trichoderma*, such as *Trichoderma reesei*, such as ones described in U.S. Pat. Nos. 6,022,725, 6,982,159, 7,045,332, 7,005,289, US 2006/0258554 US 2004/0102619. In an embodiment even a bacterial beta-glucosidase can be produced. In another embodiment the beta-glucosidase is derived from *Thielavia terrestris* (WO 2011/035029) or *Trichophaea saccata* (WO 2007/019442).

Enzymes produced by the fungus according to a process of the invention may comprise an endoglucanase (EG) from *Trichoderma*, such as *Trichoderma reesei*; from *Humicola*, such as a strain of *Humicola insolens*; from *Aspergillus*, such as *Aspergillus aculeatus* or *Aspergillus kawachii*; from *Erwinia*, such as *Erwinia carotovara*; from *Fusarium*, such as *Fusarium oxysporum*; from *Thielavia*, such as *Thielavia terrestris*; from *Humicola*, such as *Humicola grisea* var. *thermoidea* or *Humicola insolens*; from *Melanocarpus*, such as *Melanocarpus albomyces*; from *Neurospora*, such as *Neurospora crassa*; from *Myceliophthora*, such as *Myceliophthora thermophila*; from *Cladorrhinum*, such as *Cladorrhinum foecundissimum* and/or from *Chrysosporium*, such as a strain of *Chrysosporium lucknowense*. In an embodiment even a bacterial endoglucanase can be produced including, but are not limited to, *Acidothermus cellulolyticus* endoglucanase (see WO 91/05039; WO 93/15186; U.S. Pat. No. 5,275,944; WO 96/02551; U.S. Pat. No. 5,536,655, WO 00/70031, WO 05/093050); *Thermobifida fusca* endoglucanase III (see WO 05/093050); and *Thermobifida fusca* endoglucanase V (see WO 05/093050).

Enzymes produced by the fungus according to a process of the invention may comprise a cellobiohydrolase I from *Aspergillus*, such as *Aspergillus fumigatus*, such as the Cel7A CBH I disclosed in SEQ ID NO:6 in WO 2011/057140 or SEQ ID NO:6 in WO 2014/130812, or from *Trichoderma*, such as *Trichoderma reesei*.

Enzymes produced by the fungus according to a process of the invention may comprise a cellobiohydrolase II from *Aspergillus*, such as *Aspergillus fumigatus*, such as the one in SEQ ID NO:7 in WO 2014/130812 or from *Trichoderma*, such as *Trichoderma reesei*, or from *Thielavia*, such as *Thielavia terrestris*, such as cellobiohydrolase II CEL6A from *Thielavia terrestris*.

Enzymes produced by the fungus according to a process of the invention may comprise a GH61 polypeptide (a lytic polysaccharide monooxygenase) from *Thermoascus*, such as *Thermoascus aurantiacus*, such as the one described in WO 2005/074656 as SEQ ID NO:2 and SEQ ID NO:1 in WO2014/130812 and in WO 2010/065830; or from *Thielavia*, such as *Thielavia terrestris*, such as the one described in WO 2005/074647 as SEQ ID NO: 8 or SEQ ID NO:4 in WO2014/130812 and in WO 2008/148131, and WO 2011/035027; or from *Aspergillus*, such as *Aspergillus fumigatus*, such as the one described in WO 2010/138754 as SEQ ID NO:2 or SEQ ID NO: 3 in WO2014/130812; or from *Penicillium*, such as *Penicillium emersonii*, such as the one disclosed as SEQ ID NO:2 in WO 2011/041397 or SEQ ID NO:2 in WO2014/130812. Other suitable GH61 polypeptides include, but are not limited to, *Trichoderma reesei* (see WO 2007/089290), *Myceliophthora thermophila* (see WO 2009/085935, WO 2009/085859, WO 2009/085864, WO 2009/085868), *Penicillium pinophilum* (see WO 2011/005867), *Thermoascus* sp. (see WO 2011/039319), and *Thermoascus crustaceous* (see WO 2011/041504). In one aspect, the GH61 polypeptide is used in the presence of a soluble activating divalent metal cation according to WO 2008/151043, e.g. manganese sulfate. In one aspect, the GH61 polypeptide is used in the presence of a dioxy compound, a bicyclic compound, a heterocyclic compound, a nitrogen-containing compound, a quinone compound, a sulfur-containing compound, or a liquor obtained from a pretreated cellulosic material such as pretreated corn stover.

Other cellulolytic enzymes produced by the fungus according to a process of the invention are described in WO 98/13465, WO 98/015619, WO 98/015633, WO 99/06574, WO 99/10481, WO 99/025847, WO 99/031255, WO 2002/101078, WO 2003/027306, WO 2003/052054, WO 2003/052055, WO 2003/052056, WO 2003/052057, WO 2003/052118, WO 2004/016760, WO 2004/043980, WO 2004/048592, WO 2005/001065, WO 2005/028636, WO 2005/093050, WO 2005/093073, WO 2006/074005, WO 2006/117432, WO 2007/071818, WO 2007/071820, WO 2008/008070, WO 2008/008793, U.S. Pat. Nos. 5,457,046, 5,648,263, and 5,686,593, to name just a few.

In addition, examples of xylanases produced by the fungus according to a process of the invention include, but are not limited to, xylanases from *Aspergillus aculeatus* (see WO 94/21785), *Aspergillus fumigatus* (see WO 2006/078256), *Penicillium pinophilum* (see WO 2011/041405), *Penicillium* sp. (see WO 2010/126772), *Thielavia terrestris* NRRL 8126 (see WO 2009/079210), and *Trichophaea saccata* GH10 (see WO 2011/057083). Examples of beta-xylosidases produced by the fungus in the process of the invention include, but are not limited to, beta-xylosidases from *Neurospora crassa* and *Trichoderma reesei*. Examples of acetylxylan esterases produced by the fungus in the process of the invention include, but are not limited to, acetylxylan esterases from *Aspergillus aculeatus* (see WO 2010/108918), *Chaetomium globosum, Chaetomium gracile, Humicola insolens* DSM 1800 (see WO 2009/073709), *Hypocrea jecorina* (see WO 2005/001036), *Myceliophtera thermophila* (see WO 2010/014880), *Neurospora crassa, Phaeosphaeria nodorum* and *Thielavia terrestris* NRRL 8126 (see WO 2009/042846). Examples of feruloyl esterases (ferulic acid esterases) produced by the fungus in the process of the invention include, but are not limited to, feruloyl esterases form *Humicola insolens* DSM 1800 (see WO 2009/076122), *Neosartorya fischeri, Neurospora crassa, Penicillium aurantiogriseum* (see WO 2009/127729), and *Thielavia terrestris* (see WO 2010/053838 and WO 2010/065448). Examples of arabinofuranosidases produced by the fungus in the process of the invention include, but are not limited to, arabinofuranosidases from *Aspergillus niger, Humicola insolens* DSM 1800 (see WO 2006/114094 and WO 2009/073383) and *M. giganteus* (see WO 2006/114094). Examples of alpha-glucuronidases produced by the fungus in the process of the invention include, but are not limited to, alpha-glucuronidases from *Aspergillus clavatus, Aspergillus fumigatus, Aspergillus niger, Aspergillus terreus, Humicola insolens* (see WO 2010/014706), *Penicillium aurantiogriseum* (see WO 2009/068565) and *Trichoderma reesei*.

Enzymes produced by the fungus according to a process of the invention may comprise one, two, three, four classes or more of cellulase, for example one, two, three or four or all of a lytic polysaccharide monooxygenas (LPMO), an endoglucanase (EG), one or two exo-cellobiohydrolase (CBH) and a beta-glucosidase (BG). Enzymes produced by the fungus according to the process of the invention may comprise two or more of any of these classes of cellulases.

Enzymes produced by the fungus according to a process of the invention may comprise one type of cellulase activity and/or hemicellulase activity and/or pectinase activity provided by enzymes as described herein and a second type of cellulase activity and/or hemicellulase activity and/or pectinase activity provided by an additional cellulase/hemicellulase/pectinase.

As used herein, a cellulase is any enzyme which is capable of degrading or modifying cellulose. An enzyme which is capable of degrading cellulose is one which is capable of catalyzing the process of breaking down cellulose into smaller units, either partially, for example into cellodextrins, or completely into glucose monomers. A cellulase according to the invention may give rise to a mixed population of cellodextrins and glucose monomers. Such degradation will typically take place by way of a hydrolysis reaction.

Lytic polysaccharide monooxygenases (LPMO) are recently classified by CAZy in family AA9 (Auxiliary Activity Family 9) or family AA10 (Auxiliary Activity Family 10). As mentioned above, lytic polysaccharide monooxygenases are able to open a crystalline glucan structure. Lytic polysaccharide monooxygenases may also affect cello-oligosaccharides. GH61 (glycoside hydrolase family 61 or sometimes referred to EGIV) proteins are (lytic) oxygen-dependent polysaccharide monooxygenases (PMO's/LPMO's) according to the latest literature (see Isaksen et al., Journal of Biological Chemistry, vol. 289, no. 5, pp. 2632-2642). PMO and LPMO are used herein interchangeably. Often in literature these proteins are mentioned to enhance the action of cellulases on lignocellulose substrates. GH61 was originally classified as endoglucanase based on measurement of very weak endo-1,4-β-d-glucanase activity in one family member. The term "GH61" as used herein, is to be understood as a family of enzymes, which share common conserved sequence portions and folding to be classified in family 61 of the well-established CAZy GH classification system (www.cazy.org/GH61.html). The glycoside hydrolase family 61 is a member of the family of glycoside hydrolases EC 3.2.1. GH61 are recently now reclassified by CAZy in family AA9 (Auxiliary Activity Family 9). GH61 is used herein as being part of the cellulases.

CBM33 (family 33 carbohydrate-binding module) is a lytic polysaccharide monooxygenase (see Isaksen et al, Journal of Biological Chemistry, vol. 289, no. 5, pp. 2632-2642), CAZy has recently reclassified CBM33 in AA10 (Auxiliary Activity Family 10).

As used herein, a hemicellulase is any polypeptide which is capable of degrading or modifying hemicellulose. That is to say, a hemicellulase may be capable of degrading or modifying one or more of xylan, glucuronoxylan, arabinoxylan, glucomannan and xyloglucan. A polypeptide which is capable of degrading a hemicellulose is one which is capable of catalyzing the process of breaking down the hemicellulose into smaller polysaccharides, either partially, for example into oligosaccharides, or completely into sugar monomers, for example hexose or pentose sugar monomers. A hemicellulase according to the invention may give rise to a mixed population of oligosaccharides and sugar monomers. Such degradation will typically take place by way of a hydrolysis reaction.

As used herein, a pectinase is any polypeptide which is capable of degrading or modifying pectin. A polypeptide which is capable of degrading pectin is one which is capable of catalyzing the process of breaking down pectin into smaller units, either partially, for example into oligosaccharides, or completely into sugar monomers. A pectinase according to the invention may give rise to a mixed population of oligosaccharides and sugar monomers. Such degradation will typically take place by way of a hydrolysis reaction.

Accordingly, enzymes produced by the fungus according to a process of the invention may comprise any cellulase, for example, a lytic polysaccharide monooxygenase (e.g. GH61), a cellobiohydrolase, an endo-β-1,4-glucanase, a beta-glucosidase or a β-(1,3)(1,4)-glucanase.

As used herein, a cellobiohydrolase (EC 3.2.1.91) is any polypeptide which is capable of catalyzing the hydrolysis of 1,4-β-D-glucosidic linkages in cellulose or cellotetraose, releasing cellobiose from the ends of the chains. This enzyme may also be referred to as cellulase 1,4-β-cellobiosidase, 1,4-β-cellobiohydrolase, 1,4-β-D-glucan cellobiohydrolase, avicelase, exo-1,4-β-D-glucanase, exocellobiohydrolase or exoglucanase.

As used herein, an endo-β-1,4-glucanase (EC 3.2.1.4) is any polypeptide which is capable of catalyzing the endohydrolysis of 1,4-β-D-glucosidic linkages in cellulose, lichenin or cereal β-D-glucans. Such a polypeptide may also be capable of hydrolyzing 1,4-linkages in β-D-glucans also containing 1,3-linkages. This enzyme may also be referred to as cellulase, avicelase, β-1,4-endoglucan hydrolase, β-1,4-glucanase, carboxymethyl cellulase, celludextrinase, endo-1,4-β-D-glucanase, endo-1,4-β-D-glucanohydrolase, endo-1,4-β-glucanase or endoglucanase.

As used herein, a beta-glucosidase (EC 3.2.1.21) is any polypeptide which is capable of catalysing the hydrolysis of terminal, non-reducing β-D-glucose residues with release of β-D-glucose. Such a polypeptide may have a wide specificity for β-D-glucosides and may also hydrolyze one or more of the following: a β-D-galactoside, an α-L-arabinoside, a β-D-xyloside or a β-D-fucoside. This enzyme may also be referred to as amygdalase, β-D-glucoside glucohydrolase, cellobiase or gentobiase.

As used herein, a β-(1,3)(1,4)-glucanase (EC 3.2.1.73) is any polypeptide which is capable of catalysing the hydrolysis of 1,4-β-D-glucosidic linkages in β-D-glucans containing 1,3- and 1,4-bonds. Such a polypeptide may act on lichenin and cereal β-D-glucans, but not on β-D-glucans containing only 1,3- or 1,4-bonds. This enzyme may also be referred to as licheninase, 1,3-1,4-β-D-glucan 4-glucanohydrolase, β-glucanase, endo-β-1,3-1,4 glucanase, lichenase or mixed linkage β-glucanase. An alternative for this type of enzyme is EC 3.2.1.6, which is described as endo-1,3(4)-beta-glucanase. This type of enzyme hydrolyses 1,3- or 1,4-linkages in beta-D-glucanse when the glucose residue whose reducing group is involved in the linkage to be hydrolysed is itself substituted at C-3. Alternative names include endo-1,3-beta-glucanase, laminarinase, 1,3-(1,3;1,4)-beta-D-glucan 3 (4) glucanohydrolase. Substrates include laminarin, lichenin and cereal beta-D-glucans.

Enzymes produced by the fungus according to a process of the invention may comprise any hemicellulase, for example, an endoxylanase, a β-xylosidase, a α-L-arabinofuranosidase, an α-D-glucuronidase, an acetyl xylan esterase, a feruloyl esterase, a coumaroyl esterase, an α-galactosidase, a β-galactosidase, a β-mannanase or a β-mannosidase.

As used herein, an endoxylanase (EC 3.2.1.8) is any polypeptide which is capable of catalysing the endohydrolysis of 1,4-β-D-xylosidic linkages in xylans. This enzyme may also be referred to as endo-1,4-β-xylanase or 1,4-β-D-xylan xylanohydrolase. An alternative is EC 3.2.1.136, a glucuronoarabinoxylan endoxylanase, an enzyme that is able to hydrolyze 1,4 xylosidic linkages in glucuronoarabinoxylans.

As used herein, a β-xylosidase (EC 3.2.1.37) is any polypeptide which is capable of catalysing the hydrolysis of 1,4-β-D-xylans, to remove successive D-xylose residues from the non-reducing termini. Such enzymes may also hydrolyze xylobiose. This enzyme may also be referred to as xylan 1,4-β-xylosidase, 1,4-β-D-xylan xylohydrolase, exo-1,4-β-xylosidase or xylobiase.

As used herein, an α-L-arabinofuranosidase (EC 3.2.1.55) is any polypeptide which is capable of acting on α-L-arabinofuranosides, α-L-arabinans containing (1,2) and/or (1,3)- and/or (1,5)-linkages, arabinoxylans and arabinogalactans. This enzyme may also be referred to as α-N-arabinofuranosidase, arabinofuranosidase or arabinosidase.

As used herein, an α-D-glucuronidase (EC 3.2.1.139) is any polypeptide which is capable of catalysing a reaction of the following form: alpha-D-glucuronoside+H(2)O=an alcohol+D-glucuronate. This enzyme may also be referred to as alpha-glucuronidase or alpha-glucosiduronase. These enzymes may also hydrolyse 4-O-methylated glucoronic acid, which can also be present as a substituent in xylans. An alternative is EC 3.2.1.131: xylan alpha-1,2-glucuronosidase, which catalyses the hydrolysis of alpha-1,2-(4-O-methyl)glucuronosyl links.

As used herein, an acetyl xylan esterase (EC 3.1.1.72) is any polypeptide which is capable of catalysing the deacetylation of xylans and xylo-oligosaccharides. Such a polypeptide may catalyze the hydrolysis of acetyl groups from polymeric xylan, acetylated xylose, acetylated glucose, alpha-napthyl acetate or p-nitrophenyl acetate but, typically, not from triacetylglycerol. Such a polypeptide typically does not act on acetylated mannan or pectin.

As used herein, a feruloyl esterase (EC 3.1.1.73) is any polypeptide which is capable of catalysing a reaction of the form: feruloyl-saccharide+H₂O=ferulate+saccharide. The saccharide may be, for example, an oligosaccharide or a polysaccharide. It may typically catalyse the hydrolysis of the 4-hydroxy-3-methoxycinnamoyl (feruloyl) group from an esterified sugar, which is usually arabinose in 'natural' substrates. p-nitrophenol acetate and methyl ferulate are typically poorer substrates. This enzyme may also be referred to as cinnamoyl ester hydrolase, ferulic acid esterase or hydroxycinnamoyl esterase. It may also be referred to as a hemicellulase accessory enzyme, since it may help xylanases and pectinases to break down plant cell wall hemicellulose and pectin.

As used herein, a coumaroyl esterase (EC 3.1.1.73) is any polypeptide which is capable of catalysing a reaction of the form: coumaroyl-saccharide+H(2)O=coumarate+saccharide. The saccharide may be, for example, an oligosaccharide or a polysaccharide. This enzyme may also be referred to as trans-4-coumaroyl esterase, trans-p-coumaroyl esterase, p-coumaroyl esterase or p-coumaric acid esterase. This enzyme also falls within EC 3.1.1.73 so may also be referred to as a feruloyl esterase.

As used herein, an α-galactosidase (EC 3.2.1.22) is any polypeptide which is capable of catalysing the hydrolysis of terminal, non-reducing α-D-galactose residues in α-D-galactosides, including galactose oligosaccharides, galactomannans, galactans and arabinogalactans. Such a polypeptide may also be capable of hydrolyzing α-D-fucosides. This enzyme may also be referred to as melibiase.

As used herein, a β-galactosidase (EC 3.2.1.23) is any polypeptide which is capable of catalysing the hydrolysis of terminal non-reducing β-D-galactose residues in β-D-galactosides. Such a polypeptide may also be capable of hydrolyzing α-L-arabinosides. This enzyme may also be referred to as exo-(1→4)-β-D-galactanase or lactase.

As used herein, a β-mannanase (EC 3.2.1.78) is any polypeptide which is capable of catalysing the random hydrolysis of 1,4-β-D-mannosidic linkages in mannans, galactomannans and glucomannans. This enzyme may also be referred to as mannan endo-1,4-β-mannosidase or endo-1,4-mannanase.

As used herein, a β-mannosidase (EC 3.2.1.25) is any polypeptide which is capable of catalysing the hydrolysis of terminal, non-reducing β-D-mannose residues in β-D-mannosides. This enzyme may also be referred to as mannanase or mannase.

Enzymes for use in a process of the current invention may comprise any pectinase, for example an endo polygalacturonase, a pectin methyl esterase, an endo-galactanase, a beta galactosidase, a pectin acetyl esterase, an endo-pectin lyase, pectate lyase, alpha rhamnosidase, an exo-galacturonase, an expolygalacturonate lyase, a rhamnogalacturonan hydrolase, a rhamnogalacturonan lyase, a rhamnogalacturonan acetyl esterase, a rhamnogalacturonan galacturonohydrolase, a xylogalacturonase.

As used herein, an endo-polygalacturonase (EC 3.2.1.15) is any polypeptide which is capable of catalysing the random hydrolysis of 1,4-α-D-galactosiduronic linkages in pectate and other galacturonans. This enzyme may also be referred to as polygalacturonase pectin depolymerase, pectinase, endopolygalacturonase, pectolase, pectin hydrolase, pectin polygalacturonase, poly-α-1,4-galacturonide glycanohydrolase, endogalacturonase; endo-D-galacturonase or poly(1,4-α-D-galacturonide) glycanohydrolase.

As used herein, a pectin methyl esterase (EC 3.1.1.11) is any enzyme which is capable of catalysing the reaction: pectin+n H$_2$O=n methanol+pectate. The enzyme may also be known as pectinesterase, pectin demethoxylase, pectin methoxylase, pectin methylesterase, pectase, pectinoesterase or pectin pectylhydrolase.

As used herein, an endo-galactanase (EC 3.2.1.89) is any enzyme capable of catalysing the endohydrolysis of 1,4-β-D-galactosidic linkages in arabinogalactans. The enzyme may also be known as arabinogalactan endo-1,4-β-galactosidase, endo-1,4-β-galactanase, galactanase, arabinogalactanase or arabinogalactan 4-β-D-galactanohydrolase.

As used herein, a pectin acetyl esterase is defined herein as any enzyme which has an acetyl esterase activity which catalyses the deacetylation of the acetyl groups at the hydroxyl groups of GalUA residues of pectin.

As used herein, an endo-pectin lyase (EC 4.2.2.10) is any enzyme capable of catalysing the eliminative cleavage of (1→4)-α-D-galacturonan methyl ester to give oligosaccharides with 4-deoxy-6-O-methyl-α-D-galact-4-enuronosyl groups at their non-reducing ends. The enzyme may also be known as pectin lyase, pectin trans-eliminase; endo-pectin lyase, polymethylgalacturonic transeliminase, pectin methyltranseliminase, pectolyase, PL, PNL or PMGL or (1→4)-6-O-methyl-α-D-galacturonan lyase.

As used herein, a pectate lyase (EC 4.2.2.2) is any enzyme capable of catalysing the eliminative cleavage of (1→4)-α-D-galacturonan to give oligosaccharides with 4-deoxy-α-D-galact-4-enuronosyl groups at their non-reducing ends. The enzyme may also be known polygalacturonic transeliminase, pectic acid transeliminase, polygalacturonate lyase, endopectin methyltranseliminase, pectate transeliminase, endogalacturonate transeliminase, pectic acid lyase, pectic lyase, α-1,4-D-endopolygalacturonic acid lyase, PGA lyase, PPase-N, endo-α-1,4-polygalacturonic acid lyase, polygalacturonic acid lyase, pectin trans-eliminase, polygalacturonic acid trans-eliminase or (1→4)-α-D-galacturonan lyase.

As used herein, an alpha rhamnosidase (EC 3.2.1.40) is any polypeptide which is capable of catalysing the hydrolysis of terminal non-reducing α-L-rhamnose residues in α-L-rhamnosides or alternatively in rhamnogalacturonan. This enzyme may also be known as α-L-rhamnosidase T, α-L-rhamnosidase N or α-L-rhamnoside rhamnohydrolase.

As used herein, exo-galacturonase (EC 3.2.1.82) is any polypeptide capable of hydrolysis of pectic acid from the non-reducing end, releasing digalacturonate. The enzyme may also be known as exo-poly-α-galacturonosidase, exopolygalacturonosidase or exopolygalacturanosidase.

As used herein, exo-galacturonase (EC 3.2.1.67) is any polypeptide capable of catalysing: (1,4-α-D-galacturonide)$_n$+H$_2$O=(1,4-α-D-galacturonide)$_{n-1}$+D-galacturonate. The enzyme may also be known as galacturan 1,4-α-galacturonidase, exopolygalacturonase, poly(galacturonate) hydrolase, exo-D-galacturonase, exo-D-galacturonanase, exopoly-D-galacturonase or poly(1,4-α-D-galacturonide) galacturonohydrolase.

As used herein, exopolygalacturonate lyase (EC 4.2.2.9) is any polypeptide capable of catalysing eliminative cleavage of 4-(4-deoxy-α-D-galact-4-enuronosyl)-D-galacturonate from the reducing end of pectate, i.e. de-esterified pectin. This enzyme may be known as pectate disaccharide-lyase, pectate exo-lyase, exopectic acid transeliminase, exopectate lyase, exopolygalacturonic acid-trans-eliminase, PATE, exo-PATE, exo-PGL or (1-+4)-α-D-galacturonan reducing-end-disaccharide-lyase.

As used herein, rhamnogalacturonan hydrolase is any polypeptide which is capable of hydrolyzing the linkage between galactosyluronic acid and rhamnopyranosyl in an endo-fashion in strictly alternating rhamnogalacturonan structures, consisting of the disaccharide [(1,2-alpha-L-rhamnoyl-(1,4)-alpha-galactosyluronic acid].

As used herein, rhamnogalacturonan lyase is any polypeptide which is any polypeptide which is capable of cleaving α-L-Rhap-(1-+4)-α-D-GalpA linkages in an endo-fashion in rhamnogalacturonan by beta-elimination.

As used herein, rhamnogalacturonan acetyl esterase is any polypeptide which catalyzes the deacetylation of the backbone of alternating rhamnose and galacturonic acid residues in rhamnogalacturonan.

As used herein, rhamnogalacturonan galacturonohydrolase is any polypeptide which is capable of hydrolyzing galacturonic acid from the non-reducing end of strictly alternating rhamnogalacturonan structures in an exo-fashion.

As used herein, xylogalacturonase is any polypeptide which acts on xylogalacturonan by cleaving the β-xylose substituted galacturonic acid backbone in an endo-manner. This enzyme may also be known as xylogalacturonan hydrolase.

As used herein, an α-L-arabinofuranosidase (EC 3.2.1.55) is any polypeptide which is capable of acting on α-L-arabinofuranosides, α-L-arabinans containing (1,2) and/or (1,3)- and/or (1,5)-linkages, arabinoxylans and arabinogalactans. This enzyme may also be referred to as α-N-arabinofuranosidase, arabinofuranosidase or arabinosidase.

As used herein, endo-arabinanase (EC 3.2.1.99) is any polypeptide which is capable of catalysing endohydrolysis of 1,5-α-arabinofuranosidic linkages in 1,5-arabinans. The enzyme may also be known as endo-arabinase, arabinan endo-1,5-α-L-arabinosidase, endo-1,5-α-L-arabinanase, endo-α-1,5-arabanase; endo-arabanase or 1,5-α-L-arabinan 1,5-α-L-arabinanohydrolase.

Enzymes produced by the fungus according to a process of the invention will typically comprise at least two cellulases and optionally at least one hemicellulase and optionally at least one pectinase. Enzymes produced by the fungus according to a process of the invention may comprise a lytic polysaccharide monooxygenases (such as GH61), a cellobiohydrolase, an endoglucanase and/or a beta-glucosidase. Such enzymes may also comprise one or more hemicellulases and/or one or more pectinases.

In addition, one or more (for example two, three, four or all) of an amylase, a protease, a lipase, a ligninase, a hexosyltransferase, a glucuronidase, an expansin, a cellulose induced protein or a cellulose integrating protein or like protein may be produced by the fungus in the process of the invention.

"Protease" includes enzymes that hydrolyze peptide bonds (peptidases), as well as enzymes that hydrolyze bonds between peptides and other moieties, such as sugars (glycopeptidases). Many proteases are characterized under EC 3.4 and are suitable for use in the processes of the current invention. Some specific types of proteases include, cysteine proteases including pepsin, papain and serine proteases including chymotrypsins, carboxypeptidases and metalloendopeptidases.

"Lipase" includes enzymes that hydrolyze lipids, fatty acids, and acylglycerides, including phospoglycerides, lipoproteins, diacylglycerols, and the like. In plants, lipids are used as structural components to limit water loss and pathogen infection. These lipids include waxes derived from fatty acids, as well as cutin and suberin.

"Ligninase" includes enzymes that can hydrolyze or break down the structure of lignin polymers. Enzymes that can break down lignin include lignin peroxidases, manganese peroxidases, laccases and feruloyl esterases, and other enzymes described in the art known to depolymerize or otherwise break lignin polymers. Also included are enzymes capable of hydrolyzing bonds formed between hemicellulosic sugars (notably arabinose) and lignin. Ligninases include but are not limited to the following group of enzymes: lignin peroxidases (EC 1.11.1.14), manganese peroxidases (EC 1.11.1.13), laccases (EC 1.10.3.2) and feruloyl esterases (EC 3.1.1.73).

"Hexosyltransferase" (2.4.1.-) includes enzymes which are capable of catalysing a transferase reaction, but which can also catalyze a hydrolysis reaction, for example of cellulose and/or cellulose degradation products. An example of a hexosyltransferase which may be used in the invention is a β-glucanosyltransferase. Such an enzyme may be able to catalyze degradation of (1,3)(1,4)glucan and/or cellulose and/or a cellulose degradation product.

"Glucuronidase" includes enzymes that catalyze the hydrolysis of a glucoronoside, for example β-glucuronoside to yield an alcohol. Many glucuronidases have been characterized and may be suitable for use in the invention, for example β-glucuronidase (EC 3.2.1.31), hyaluronoglucuronidase (EC 3.2.1.36), glucuronosyl-disulfoglucosamine glucuronidase (3.2.1.56), glycyrrhizinate β-glucuronidase (3.2.1.128) or α-D-glucuronidase (EC 3.2.1.139).

Enzymes for use in a process of the current invention may comprise an expansin or expansin-like protein, such as a swollenin (see Salheimo et al., Eur. J. Biochem. 269, 4202-4211, 2002) or a swollen in-like protein.

Expansins are implicated in loosening of the cell wall structure during plant cell growth. Expansins have been proposed to disrupt hydrogen bonding between cellulose and other cell wall polysaccharides without having hydrolytic activity. In this way, they are thought to allow the sliding of cellulose fibers and enlargement of the cell wall. Swollenin, an expansin-like protein contains an N-terminal Carbohydrate Binding Module Family 1 domain (CBD) and a C-terminal expansin-like domain. For the purposes of this invention, an expansin-like protein or swollenin-like protein may comprise one or both of such domains and/or may disrupt the structure of cell walls (such as disrupting cellulose structure), optionally without producing detectable amounts of reducing sugars.

Enzymes produced by the fungus according to a process of the invention may comprise a cellulose induced protein, for example the polypeptide product of the cip1 or cip2 gene or similar genes (see Foreman et al., J. Biol. Chem. 278(34), 31988-31997, 2003), a cellulose/cellulosome integrating protein, for example the polypeptide product of the cipA or cipC gene, or a scaffoldin or a scaffoldin-like protein. Scaffoldins and cellulose integrating proteins are multifunctional integrating subunits which may organize cellulolytic subunits into a multi-enzyme complex. This is accomplished by the interaction of two complementary classes of domain, i.e. a cohesion domain on scaffoldin and a dockerin domain on each enzymatic unit. The scaffoldin subunit also bears a cellulose-binding module (CBM) that mediates attachment of the cellulosome to its substrate. A scaffoldin or cellulose integrating protein for the purposes of this invention may comprise one or both of such domains.

Enzymes produced by the fungus according to a process of the invention may also comprise a catalase. The term "catalase" means a hydrogen-peroxide: hydrogen-peroxide oxidoreductase (EC 1.11.1.6 or EC 1.11.1.21) that catalyzes the conversion of two hydrogen peroxides to oxygen and two waters. Catalase activity can be determined by monitoring the degradation of hydrogen peroxide at 240 nm based on the following reaction: $2H_2O_2 \rightarrow 2H_2O+O_2$. The reaction is conducted in 50 mM phosphate pH 7.0 at 25° C. with 10.3 mM substrate ($H_2O_2$) and approximately 100 units of enzyme per ml. Absorbance is monitored spectrophotometrically within 16-24 seconds, which should correspond to an absorbance reduction from 0.45 to 0.4. One catalase activity unit can be expressed as one micromole of $H_2O_2$ degraded per minute at pH 7.0 and 25° C.

Enzymes produced by the fungus according to a process of the invention may comprise a member of each of the classes of enzymes mentioned above, several members of one enzyme class, or any combination of these enzymes classes or helper proteins (i.e. those proteins mentioned herein which do not have enzymatic activity per se, but do nevertheless assist in lignocellulosic degradation).

In the process for degrading a cellulosic substrate as described herein and in the process for producing a fermentation product from a cellulosic substrate as described herein, the enzymes described above may be provided concomitantly (i.e. in a single composition of polypeptides) or separately or sequentially.

The invention also relates to a process for degrading a cellulosic substrate, the process comprising the steps of:
a) performing a process for producing a fermentation product according to the present invention (see above), and
b) adding the enzyme or enzyme composition produced in step (c) and/or step (g) and/or step (k) to the cellulosic substrate to degrade the cellulosic substrate.

The invention also relates to a process for hydrolysing a cellulosic substrate, the process comprising the steps of:
a) performing a process for producing a fermentation product according to the present invention, and
b) adding the enzyme or enzyme composition produced in step (c) and/or step (g) and/or step (k) to the cellulosic substrate to hydrolyse the cellulosic substrate.

The invention also relates to a process for producing a sugar product from a cellulosic substrate, which process comprises the steps of:
a) performing a process for producing a fermentation product according to the present invention, and
b) adding the enzyme or enzyme composition produced in step (c) and/or step (g) and/or step (k) to the cellulosic substrate to produce the sugar product from the cellulosic substrate.

In general, in the enzymatic hydrolysis several enzymes are used, i.e. several enzymes with different cellulolytic activities are used. These enzymes can be any of the enzymes described above or any combination thereof. They can be either produced by the enzyme production process as described herein. The fungus can produce only one of these enzymes, but also more than one, i.e. two, three, four or even more enzymes. If not all of the enzymes necessary for the enzymatric hydrolysis are produced by the fungus, the remaining enzymes can be added after culturing. They may also be added to the cellulosic substrate during enzymatic hydrolysis. The term "enzymatic hydrolysis of a cellulosic substrate" and "degradation of a cellulosic substrate" can be used interchangeably herein.

In an embodiment the cellulosic substrate is subjected to at least one solid/liquid separation before the enzymatic hydrolysis. In an embodiment the cellulosic substrate is subjected to pretreatment and at least one solid/liquid separation before the enzymatic hydrolysis. So, before subjecting the cellulosic substrate and/or pretreated cellulosic substrate to enzymatic hydrolysis, it can be subjected to at least one solid/liquid separation. The process and conditions of solid/liquid separation will depend on the type of cellulosic substrate used and are well within the scope of the skilled artisan. Examples include, but are not limited to, centrifugation, cyclonic separation, filtration, decantation, sieving and sedimentation. During solid/liquid separation, means and/or aids for improving the separation may be used.

In an embodiment the cellulosic substrate is lignocellulosic material. Lignocellulosic material as used herein includes any lignocellulosic and/or hemicellulosic material. Lignocellulosic material suitable for use in the processes of the current invention includes biomass, e.g. virgin biomass and/or non-virgin biomass such as agricultural biomass, commercial organics, construction and demolition debris, municipal solid waste, waste paper and yard waste. Common forms of biomass include trees, shrubs and grasses, wheat, wheat straw, sugar cane, cane straw, sugar cane bagasse, switch grass, miscanthus, energy cane, corn, corn stover, corn fiber, corn husks, corn cobs, canola stems, soybean stems, sweet sorghum, distillers dried grains, corn kernel including fiber from kernels, products and by-products from milling of grains such as corn, wheat and barley (including wet milling and dry milling) often called "bran or fibre" as well as municipal solid waste, waste paper and yard waste. The biomass can also be, but is not limited to, herbaceous material, agricultural residues, forestry residues, municipal solid wastes, waste paper, and pulp and paper mill residues. "Agricultural biomass" includes branches, bushes, canes, corn and corn husks, energy crops, forests, fruits, flowers, grains, grasses, herbaceous crops, leaves, bark, needles, logs, roots, saplings, short rotation woody crops, shrubs, switch grasses, trees, vegetables, fruit peels, vines, sugar beet pulp, wheat midlings, oat hulls, and hard and soft woods (not including woods with deleterious materials). In addition, agricultural biomass includes organic waste materials generated from agricultural processes including farming and forestry activities, specifically including forestry wood waste. Agricultural biomass may be any of the aforementioned singularly or in any combination or mixture thereof. In a preferred embodiment the lignocellulosic material is sugar cane bagasse or sugar cane straw.

In an embodiment the cellulosic substrate is pretreated before and/or during the enzymatic hydrolysis. Pretreatment processes are known in the art and include, but are not limited to, heat, mechanical, chemical modification, biological modification and any combination thereof. Pretreatment is typically performed in order to enhance the accessibility of the cellulosic substrate to enzymatic hydrolysis and/or hydrolyse the hemicellulose and/or solubilize the hemicellulose and/or cellulose and/or lignin, in the cellulosic substrate. In an embodiment, the pretreatment comprises treating the cellulosic substrate with steam explosion, hot water treatment or treatment with dilute acid or dilute base. Examples of pretreatment processes include, but are not limited to, steam treatment (e.g. treatment at 100-260° C., at a pressure of 7-45 bar, at neutral pH, for 1-10 minutes), dilute acid treatment (e.g. treatment with 0.1-5% $H_2SO_4$ and/or $SO_2$ and/or $HNO_3$ and/or HCl, in presence or absence of steam, at 120-200° C., at a pressure of 2-15 bar, at acidic pH, for 2-30 minutes), organosolv treatment (e.g. treatment with 1-1.5% $H_2SO_4$ in presence of organic solvent and steam, at 160-200° C., at a pressure of 7-30 bar, at acidic pH, for 30-60 minutes), lime treatment (e.g. treatment with 0.1-2% $NaOH/Ca(OH)_2$ in the presence of water/steam at 60-160° C., at a pressure of 1-10 bar, at alkaline pH, for 60-4800 minutes), ARP treatment (e.g. treatment with 5-15% $NH_3$, at 150-180° C., at a pressure of 9-17 bar, at alkaline pH, for 10-90 minutes), AFEX treatment (e.g. treatment with >15% $NH_3$, at 60-140° C., at a pressure of 8-20 bar, at alkaline pH, for 5-30 minutes).

The cellulosic substrate may be washed. In an embodiment the cellulosic substrate may be washed before and/or after the pretreatment. The washing step may be performed before and/or after solid/liquid separation of the cellulosic substrate and/or the pretreated cellulosic substrate. If performed after the solid/liquid separation, the solid fraction obtained after solid/liquid separation may be washed. The washing step may be used to remove water soluble compounds that may act as inhibitors for the fermentation and/or hydrolysis step. The washing step may be conducted in manner known to the skilled person. Next to washing, other detoxification processes do exist. The pretreated cellulosic substrate may also be detoxified by any (or any combination) of these processes which include, but are not limited to, solid/liquid separation, vacuum evaporation, extraction, adsorption, neutralization, overliming, addition of reducing agents, addition of detoxifying enzymes such as laccases or peroxidases, addition of microorganisms capable of detoxification of hydrolysates.

In an embodiment the enzymatically hydrolysed cellulosic substrate is subjected to a solid/liquid separation to obtain a solid fraction and a liquid fraction. Processes for solid/liquid separation include, but are not limited to, centrifugation, cyclonic separation, filtration, decantation, sieving and sedimentation. During solid/liquid separation, means and/or aids may be used to improve the separation.

In an embodiment a part of the enzymatically hydrolysed cellulosic substrate is used in the process for producing a fermentation product as described herein. The enzymatically hydrolysed cellulosic substrate that is added to the fungus before and/or during culturing can be concentrated before addition.

In an embodiment the part of the enzymatically hydrolysed cellulosic substrate, that is used in the process for producing a fermentation product as described herein, has been subjected to a solid/liquid separation. In an embodiment the liquid fraction obtained after solid/liquid separation of the enzymatically hydrolysed cellulosic substrate may be used in the process for producing a fermentation product as described herein. In an embodiment that liquid fraction may be subjected to a concentration step, before it is used in the fermentation product production process.

In an embodiment a part of the enzymatically hydrolysed cellulosic substrate and a part of the cellulosic substrate and/or the pretreated cellulosic substrate are used in the process for producing a fermentation product as described herein. This means that a part of the enzymatically hydrolysed cellulosic substrate and/or a part of the cellulosic substrate and/or the pretreated cellulosic substrate is added to the fungus before and/or during culturing. In an embodiment the cellulosic substrate and/or the pretreated cellulosic substrate used has not undergone enzymatic hydrolysis and/or has not been subjected to a solid/liquid separation.

The cellulosic substrate and/or the pretreated cellulosic substrate that is added to the fungus before and/or during culturing can be washed before addition.

In an alternative embodiment, when the enzymatic hydrolysis comprises a separate liquefaction step and saccharification step (as described in more detail below), the product of the liquefaction step can be used in the culturing of the fungus. This can be done with or without addition of enzymatically hydrolysed cellulosic substrate. Of course, also each and every combination of part of the enzymatically hydrolysed cellulosic substrate, part of the pretreated cellulosic substrate, product of the liquefaction step and external carbon and nutrient source can be used in the culturing of the fungus.

In an embodiment the enzymatic hydrolysis comprises at least a liquefaction step wherein the cellulosic substrate and/or the pretreated cellulosic substrate is hydrolysed in at least a first container, and a saccharification step wherein the liquefied material is hydrolysed in the at least first container and/or in at least a second container. Saccharification can be done in the same container as the liquefaction (i.e. the at least first container), it can also be done in a separate container (i.e. at least a second container). So, in the enzymatic hydrolysis liquefaction and saccharification may be combined. Alternatively, the liquefaction and saccharification may be separate steps. Liquefaction and saccharification may be performed at different temperatures, but may also be performed at a single temperature. In an embodiment the temperature of the liquefaction is higher than the temperature of the saccharification. Liquefaction is preferably carried out at a temperature of 60-75° C. and saccharification is preferably carried out at a temperature of 50-65° C.

Enzymes are present in the liquefaction step and in the saccharification step of the enzymatic hydrolysis. These enzymes may be the same or may be different. Furthermore, as described above, additional enzymes are added during the liquefaction step and the saccharification step. The enzymes added may be enzymes that are already present in the liquefaction step and in the saccharification step. Alternatively, they may be different enzymes. Moreover, the additional enzymes added during the liquefaction step may differ or may be the same as the additional enzymes added during the saccharification step.

The enzymatic hydrolysis can be performed in one or more hydrolysis reactors, but can also be performed in one or more tubes or any other continuous system. This also holds true when the enzymatic hydrolysis comprises a liquefaction step and a saccharification step. The liquefaction step can be performed in one or more hydrolysis reactors, but can also be performed in one or more tubes or any other continuous system and/or the saccharification step can be performed in one or more hydrolysis reactors, but can also be performed in one or more tubes or any other continuous system. Examples of containers to be used in the present invention include, but are not limited to, fed-batch stirred containers, batch stirred containers, continuous flow stirred containers with ultrafiltration, and continuous plug-flow column reactors. Stirring can be done by one or more impellers, pumps and/or static mixers.

In an embodiment the cellulosic substrate and/or the pretreated cellulosic substrate can be added to the one or more hydrolysis reactors used for the enzymatic hydrolysis. In an embodiment the enzymes used in the enzymatic hydrolysis are already present in the one or more hydrolysis reactors before the cellulosic substrate and/or the pretreated cellulosic substrate is added. In another embodiment the enzymes used in the enzymatic hydrolysis can be added to the one or more hydrolysis reactors. In an embodiment the cellulosic substrate and/or the pretreated cellulosic substrate is already present in the one or more hydrolysis reactors before the enzymes used in the enzymatic hydrolysis are added. In an embodiment both the cellulosic substrate and/or the pretreated cellulosic substrate and the enzymes used in the enzymatic hydrolysis are added simultaneously to the one or more hydrolysis reactors. The enzymes used in the enzymatic hydrolysis may be an aqueous composition. This paragraph also holds true when the enzymatic hydrolysis comprises a liquefaction step and a saccharification step.

The enzymes used in the enzymatic hydrolysis may be added before and/or during the enzymatic hydrolysis. As indicated above, when the cellulosic substrate and/or the pretreated cellulosic substrate is subjected to a solid/liquid separation before enzymatic hydrolysis, the enzymes used in the enzymatic hydrolysis may be added before the solid/liquid separation. Alternatively, they may also be added after solid/liquid separation or before and after solid/liquid separation. The enzymes may also be added during the enzymatic hydrolysis. In case the enzymatic hydrolysis comprises a liquefaction step and saccharification step, additional enzymes may be added during and/or after the liquefaction step. The additional enzymes may be added before and/or during the saccharification step. Additional enzymes may also be added after the saccharification step.

Significantly, a process for degrading cellulosic substrate of the invention may be carried out using high levels of dry matter (of the cellulosic substrate) in the hydrolysis reaction. In an embodiment the dry matter content at the end of the enzymatic hydrolysis is 5 wt % or higher, 6 wt % or higher, 7 wt % or higher, 8 wt % or higher, 9 wt % or higher, 10 wt % or higher, 11 wt % or higher, 12 wt % or higher, 13 wt % or higher, 14 wt % or higher, 15 wt % or higher, 16 wt % or higher, 17 wt % or higher, 18 wt % or higher, 19 wt % or higher, 20 wt % or higher, 21 wt % or higher, 22 wt % or higher, 23 wt % or higher, 24 wt % or higher, 25 wt % or higher, 26 wt % or higher, 27 wt % or higher, 28 wt % or higher, 29 wt % or higher, 30 wt % or higher, 31 wt % or higher, 32 wt % or higher, 33 wt % or higher, 34 wt % or higher, 35 wt % or higher, 36 wt % or higher, 37 wt % or higher, 38 wt % or higher or 39 wt % or higher. In an embodiment the dry matter content at the end of the enzymatic hydrolysis is between 5 wt %-40 wt %, 6 wt %-40 wt %, 7 wt %-40 wt %, 8 wt %-40 wt %, 9 wt %-40 wt %, 10 wt %-40 wt %, 11 wt %-40 wt %, 12 wt %-40 wt %, 13 wt %-40 wt %, 14 wt %-40 wt %, 15 wt %-40 wt %, 16 wt %-40 wt %, 17 wt %-40 wt %, 18 wt %-40 wt %, 19 wt %-40 wt %, 20 wt %-40 wt %, 21 wt %-40 wt %, 22 wt %-40 wt %, 23 wt %-40 wt %, 24 wt %-40 wt %, 25 wt %-40 wt %, 26 wt %-40 wt %, 27 wt %-40 wt %, 28 wt %-40 wt %, 29 wt %-40 wt %, 30 wt %-40 wt %, 31 wt %-40 wt %, 32 wt %-40 wt %, 33 wt %-40 wt %, 34 wt %-40 wt %, 35 wt %-40 wt %, 36 wt %-40 wt %, 37 wt %-40 wt %, 38 wt %-40 wt %, 39 wt %-40 wt %.

In an embodiment the dry matter content at the end of the liquefaction step of the enzymatic hydrolysis is 5 wt % or higher, 6 wt % or higher, 7 wt % or higher, 8 wt % or higher, 9 wt % or higher, 10 wt % or higher, 11 wt % or higher, 12 wt % or higher, 13 wt % or higher, 14 wt % or higher, 15 wt % or higher, 16 wt % or higher, 17 wt % or higher, 18 wt % or higher, 19 wt % or higher, 20 wt % or higher, 21 wt % or higher, 22 wt % or higher, 23 wt % or higher, 24 wt % or higher, 25 wt % or higher, 26 wt % or higher, 27 wt % or higher, 28 wt % or higher, 29 wt % or higher, 30 wt % or higher, 31 wt % or higher, 32 wt % or higher, 33 wt % or higher, 34 wt % or higher, 35 wt % or higher, 36 wt % or higher, 37 wt % or higher, 38 wt % or higher or 39 wt % or higher. In an embodiment the dry matter content at the end of the liquefaction step of the enzymatic hydrolysis is between 5 wt %-40 wt %, 6 wt %-40 wt %, 7 wt %-40 wt %, 8 wt %-40 wt %, 9 wt %-40 wt %, 10 wt %-40 wt %, 11 wt %-40 wt %, 12 wt %-40 wt %, 13 wt %-40 wt %, 14 wt %-40 wt %, 15 wt %-40 wt %, 16 wt %-40 wt %, 17 wt %-40 wt %, 18 wt %-40 wt %, 19 wt %-40 wt %, 20 wt %-40 wt %, 21 wt %-40 wt %, 22 wt %-40 wt %, 23 wt %-40 wt %, 24 wt %-40 wt %, 25 wt %-40 wt %, 26 wt %-40 wt %, 27 wt %-40 wt %, 28 wt %-40 wt %, 29 wt %-40 wt %, 30 wt %-40 wt %, 31 wt %-40 wt %, 32 wt %-40 wt %, 33 wt %-40 wt %, 34 wt %-40 wt %, 35 wt %-40 wt %, 36 wt %-40 wt %, 37 wt %-40 wt %, 38 wt %-40 wt %, 39 wt %-40 wt %.

In an embodiment the dry matter content at the end of the saccharification step of the enzymatic hydrolysis is 5 wt % or higher, 6 wt % or higher, 7 wt % or higher, 8 wt % or higher, 9 wt % or higher, 10 wt % or higher, 11 wt % or higher, 12 wt % or higher, 13 wt % or higher, 14 wt % or higher, 15 wt % or higher, 16 wt % or higher, 17 wt % or higher, 18 wt % or higher, 19 wt % or higher, 20 wt % or higher, 21 wt % or higher, 22 wt % or higher, 23 wt % or higher, 24 wt % or higher, 25 wt % or higher, 26 wt % or higher, 27 wt % or higher, 28 wt % or higher, 29 wt % or higher, 30 wt % or higher, 31 wt % or higher, 32 wt % or higher, 33 wt % or higher, 34 wt % or higher, 35 wt % or higher, 36 wt % or higher, 37 wt % or higher, 38 wt % or higher or 39 wt % or higher. In an embodiment the dry matter content at the end of the saccharification step of the enzymatic hydrolysis is between 5 wt %-40 wt %, 6 wt %-40 wt %, 7 wt %-40 wt %, 8 wt %-40 wt %, 9 wt %-40 wt %, 10 wt %-40 wt %, 11 wt %-40 wt %, 12 wt %-40 wt %, 13 wt %-40 wt %, 14 wt %-40 wt %, 15 wt %-40 wt %, 16 wt %-40 wt %, 17 wt %-40 wt %, 18 wt %-40 wt %, 19 wt %-40 wt %, 20 wt %-40 wt %, 21 wt %-40 wt %, 22 wt %-40 wt %, 23 wt %-40 wt %, 24 wt %-40 wt %, 25 wt %-40 wt %, 26 wt %-40 wt %, 27 wt %-40 wt %, 28 wt %-40 wt %, 29 wt %-40 wt %, 30 wt %-40 wt %, 31 wt %-40 wt %, 32 wt %-40 wt %, 33 wt %-40 wt %, 34 wt %-40 wt %, 35 wt %-40 wt %, 36 wt %-40 wt %, 37 wt %-40 wt %, 38 wt %-40 wt %, 39 wt %-40 wt %.

In an embodiment the total enzymatic hydrolysis time is 10 hours or more, 12 hours or more, 14 hours or more, 16 hours or more, 18 hours or more, 20 hours or more, 30 hours or more, 40 hours or more, 50 hours or more, 60 hours or more, 70 hours or more, 80 hours or more, 90 hours or more, 100 hours or more, 110 hours or more, 120 hours or more, 130 hours or more, 140 hours or more, 150 hours or more, 160 hours or more, 170 hours or more, 180 hours or more, 190 hours or more, 200 hours or more.

In an embodiment, the total enzymatic hydrolysis time is 10 to 300 hours, 16 to 275 hours, preferably 20 to 250 hours, more preferably 30 to 200 hours, most preferably 40 to 150 hours.

The viscosity of the cellulosic substrate in the one or more hydrolysis reactors used for the enzymatic hydrolysis is kept between 10 and 4000 cP, between 10 and 2000 cP, preferably between 10 and 1000 cP. The viscosity can be determined with a Brookfield DV III Rheometer at the temperature used for the hydrolysis.

In an embodiment oxygen is added during the enzymatic hydrolysis. In an embodiment oxygen is added during at least a part of the enzymatic hydrolysis. Oxygen can be added continuously or discontinuously during the enzymatic hydrolysis. In an embodiment oxygen is added one or more times during the enzymatic hydrolysis. In an embodiment oxygen may be added before the enzymatic hydrolysis, during the addition of cellulosic substrate to a hydrolysis reactor used of enzymatic hydrolysis, during the addition of enzyme to a hydrolysis reactor used of enzymatic hydrolysis, during a part of the enzymatic hydrolysis, during the whole enzymatic hydrolysis or any combination thereof. Oxygen is added to the one or more hydrolysis reactors used in the enzymatic hydrolysis.

Oxygen can be added in several forms. For example, oxygen can be added as oxygen gas, oxygen-enriched gas, such as oxygen-enriched air, or air. Oxygen may also be added by means of in situ oxygen generation.

Examples how to add oxygen include, but are not limited to, addition of oxygen by means of sparging, electrolysis, chemical addition of oxygen, filling the one or more hydrolysis reactors used in the enzymatic hydrolysis from the top (plunging the hydrolysate into the tank and consequently introducing oxygen into the hydrolysate) and addition of oxygen to the headspace of said one or more hydrolysis reactors. When oxygen is added to the headspace of the hydrolysis reactor(s), sufficient oxygen necessary for the hydrolysis reaction may be supplied. In general, the amount of oxygen added to the hydrolysis reactor(s) can be controlled and/or varied. Restriction of the oxygen supplied is possible by adding only oxygen during part of the hydrolysis time in said hydrolysis reactor(s). Another option is adding oxygen at a low concentration, for example by using a mixture of air and recycled air (air leaving the hydrolysis reactor) or by "diluting" air with an inert gas. Increasing the amount of oxygen added can be achieved by addition of oxygen during longer periods of the hydrolysis time, by adding the oxygen at a higher concentration or by adding more air. Another way to control the oxygen concentration is to add an oxygen consumer and/or an oxygen generator. Oxygen can be introduced, for example blown, into the liquid hydrolysis reactor contents of cellulosic substrate. It can also be blown into the headspace of the hydrolysis reactor.

In an embodiment oxygen is added to the one or more hydrolysis reactors used in the enzymatic hydrolysis before and/or during and/or after the addition of the cellulosic substrate and/or the pretreated cellulosic substrate to said one or more hydrolysis reactors. The oxygen may be introduced together with the cellulosic substrate and/or the pretreated cellulosic substrate that enters the hydrolysis reactor(s). The oxygen may be introduced into the material stream that will enter the hydrolysis reactor(s) or with part of the hydrolysis reactor contents that passes an external loop of the hydrolysis reactor(s).

In an embodiment the hydrolysis reactors used in the enzymatic hydrolysis have a volume of at least 1 $m^3$. Preferably, the containers have a volume of at least 1 $m^3$, at least 2 $m^3$, at least 3 $m^3$, at least 4 $m^3$, at least 5 $m^3$, at least 6 $m^3$, at least 7 $m^3$, at least 8 $m^3$, at least 9 $m^3$, at least 10 $m^3$, at least 15 $m^3$, at least 20 $m^3$, at least 25 $m^3$, at least 30 $m^3$, at least 35 $m^3$, at least 40 $m^3$, at least 45 $m^3$, at least 50 $m^3$, at least 60 $m^3$, at least 70 $m^3$, at least 75 $m^3$, at least 80 $m^3$, at least 90 $m^3$, at least 100 $m^3$, at least 200 $m^3$, at least 300 $m^3$, at least 400 $m^3$, at least 500 $m^3$, at least 600 $m^3$, at least 700 $m^3$, at least 800 $m^3$, at least 900 $m^3$, at least 1000 $m^3$, at least 1500 $m^3$, at least 2000 $m^3$, at least 2500 $m^3$. In general, the hydrolysis reactors will be smaller than 3000 $m^3$ or 5000 $m^3$. In case several hydrolysis reactors are used in the enzymatic hydrolysis, they may have the same volume, but also may have a different volume. In case the enzymatic hydrolysis comprises a separate liquefaction step and saccharification step the hydrolysis reactors used for the liquefaction step and the hydrolysis reactors used for the saccharification step may have the same volume, but also may have a different volume.

The invention also relates to process for producing a fermentation product from a cellulosic substrate, the process comprising the steps of:
a) performing a process for producing a fermentation product according to the present invention (see above), and
b) adding the enzyme or enzyme composition produced in step (c) and/or step (g) and/or step (k) to the cellulosic substrate to degrade the cellulosic substrate, and
c) fermenting the degraded cellulosic substrate by a fermenting microorganism to obtain the fermentation product.

All features and embodiments as described above for the process for producing a fermentation product and all features and embodiments as described above for the process for degrading a cellulosic substrate do also apply for the process for producing a fermentation product from a cellulosic substrate.

In an embodiment enzymatic hydrolysis and fermentation may be separate steps, but may also be combined. Examples include, but are not limited to, separate hydrolysis and fermentation (SHF), simultaneous saccharification and fermentation (SSF), simultaneous saccharification and co-fermentation (SSCF), hybrid hydrolysis and fermentation (HHF), separate hydrolysis and co-fermentation (SHCF), hybrid hydrolysis and co-fermentation (HHCF), and direct microbial conversion (DMC), also sometimes called consolidated bioprocessing (CBP).

In an embodiment the reactors used in step of fermenting the degraded cellulosic substrate have a volume of at least 1 $m^3$. Preferably, the reactors have a volume of at least 1 $m^3$, at least 2 $m^3$, at least 3 $m^3$, at least 4 $m^3$, at least 5 $m^3$, at least 6 $m^3$, at least 7 $m^3$, at least 8 $m^3$, at least 9 $m^3$, at least 10 $m^3$, at least 15 $m^3$, at least 20 $m^3$, at least 25 $m^3$, at least 30 $m^3$, at least 35 $m^3$, at least 40 $m^3$, at least 45 $m^3$, at least 50 $m^3$, at least 60 $m^3$, at least 70 $m^3$, at least 75 $m^3$, at least 80 $m^3$, at least 90 $m^3$, at least 100 $m^3$, at least 200 $m^3$, at least 300 $m^3$, at least 400 $m^3$, at least 500 $m^3$, at least 600 $m^3$, at least 700 $m^3$, at least 800 $m^3$, at least 900 $m^3$, at least 1000 $m^3$, at least 1500 $m^3$, at least 2000 $m^3$, at least 2500 $m^3$, at least 3000 $m^3$, at least 3500 $m^3$, at least 4000 $m^3$, at least 4500 $m^3$. In general, the reactors will be smaller than 5000 $m^3$.

In an embodiment the fermentation step is performed in one or more reactors. The fermentation can be done in the same reactor(s) wherein the enzymatic hydrolysis is performed.

In an embodiment the fermentation is a step in which a fermenting microorganism is used for the fermentation of a carbon source comprising sugar(s), e.g. glucose, L-arabinose and/or xylose. The carbon source may include any carbohydrate oligo- or polymer comprising L-arabinose, xylose or glucose units, such as e.g. lignocellulose, xylans, cellulose, starch, arabinan and the like. For release of xylose or glucose units from such carbohydrates, appropriate carbohydrases (such as xylanases, glucanases, amylases and the like) may be added to the fermentation medium or may be produced by the modified host cell. In the latter case, the modified host cell may be genetically engineered to produce and excrete such carbohydrases. An additional advantage of using oligo- or polymeric sources of glucose is that it enables to maintain a low(er) concentration of free glucose during the fermentation, e.g. by using rate-limiting amounts of the carbohydrases. This, in turn, will prevent repression of systems required for metabolism and transport of non-glucose sugars such as xylose. In a preferred process the modified host cell ferments both the L-arabinose (optionally xylose) and glucose, preferably simultaneously in which case preferably a modified host cell is used which is insensitive to glucose repression to prevent diauxic growth. In addition to a source of L-arabinose, optionally xylose (and glucose) as carbon source, the fermentation medium will further comprise the appropriate ingredient required for growth of the modified host cell. Compositions of fermentation media for growth of microorganisms such as yeasts or filamentous fungi are well known in the art.

The fermentation process may be an aerobic or an anaerobic fermentation process. An anaerobic fermentation process is herein defined as a fermentation process run in the absence of oxygen or in which substantially no oxygen is consumed, preferably less than 5, 2.5 or 1 mmol/L/h, more preferably 0 mmol/L/h is consumed (i.e. oxygen consumption is not detectable), and wherein organic molecules serve as both electron donor and electron acceptors. In the absence of oxygen, NADH produced in glycolysis and biomass formation, cannot be oxidised by oxidative phosphorylation. To solve this problem many microorganisms use pyruvate or one of its derivatives as an electron and hydrogen acceptor thereby regenerating $NAD^+$. Thus, in a preferred anaerobic fermentation process pyruvate is used as an electron (and hydrogen acceptor) and is reduced to fermentation products such as ethanol, lactic acid, 3-hydroxy-propionic acid, acrylic acid, acetic acid, succinic acid, citric acid, malic acid, fumaric acid, an amino acid, 1,3-propane-diol, ethylene, glycerol, butanol, a β-lactam antibiotic and a cephalosporin. In a preferred embodiment, the fermentation process is anaerobic. An anaerobic process is advantageous, since it is cheaper than aerobic processes: less special equipment is needed. Furthermore, anaerobic processes are expected to give a higher product yield than aerobic processes. Under aerobic conditions, usually the biomass yield is higher than under anaerobic conditions. As a consequence, usually under aerobic conditions, the expected product yield is lower than under anaerobic conditions.

In another embodiment, the fermentation process is under oxygen-limited conditions. More preferably, the fermentation process is aerobic and under oxygen-limited conditions. An oxygen-limited fermentation process is a process in which the oxygen consumption is limited by the oxygen transfer from the gas to the liquid. The degree of oxygen limitation is determined by the amount and composition of the ingoing gas flow as well as the actual mixing/mass transfer properties of the fermentation equipment used. Preferably, in a process under oxygen-limited conditions, the rate of oxygen consumption is at least 5.5, more preferably at least 6 and even more preferably at least 7 mmol/L/h.

The fermentation process is preferably run at a temperature that is optimal for the modified cell. Thus, for most yeasts or fungal cells, the fermentation process is performed at a temperature which is less than 42° C., preferably 38° C. or lower. For yeast or filamentous fungal host cells, the fermentation process is preferably performed at a temperature which is lower than 35, 33, 30 or 28° C. and at a temperature which is higher than 20, 22, or 25° C. In an embodiment the alcohol fermentation step and the organic acid fermentation step are performed between 25° C. and 35° C.

In an embodiment of the invention, the fermentation is conducted with a fermenting microorganism. In an embodiment the fermenting microorganism is an alcohol producing microorganisms. In an embodiment the fermentation is performed in one or more reactors. In an embodiment the alcohol producing microorganism is a microorganism that is able to ferment at least one C5 sugar. Preferably, it is also able to ferment at least one C6 sugar. The alcohol producing microorganisms may be a prokaryotic or eukaryotic organism. The microorganism used in the process may be a genetically engineered microorganism. Examples of suitable alcohol producing organisms are yeasts, for instance *Saccharomyces*, e.g. *Saccharomyces cerevisiae, Saccharomyces pastorianus* or *Saccharomyces uvarum, Hansenula, Issatchenkia*, e.g. *Issatchenkia orientalis, Pichia*, e.g. *Pichia stipites* or *Pichia pastoris, Kluyveromyces*, e.g. *Kluyveromyces fagilis, Candida*, e.g. *Candida pseudotropicalis* or *Candida acidothermophilum, Pachysolen*, e.g. *Pachysolen tannophilus* or bacteria, for instance *Lactobacillus*, e.g. *Lactobacillus lactis, Geobacillus, Zymomonas*, e.g. *Zymomonas mobilis, Clostridium*, e.g. *Clostridium phytofermentans, Escherichia*, e.g. *E. coli, Klebsiella*, e.g. *Klebsiella oxytoca*. Commercially available yeast suitable for ethanol production include, but are not limited to, BIOFERM™ AFT and XR (NABC—North American Bioproducts Corporation, GA, USA), ETHANOL RED™ yeast (Fermentis/Lesaffre, USA), FALI™ (Fleischmann's Yeast, USA), FERMIOL™ (DSM Specialties), GERT STRAND™ (Gert Strand AB, Sweden), and SUPERSTART™ and THERMOSACC™ fresh yeast (Ethanol Technology, WI, USA). In an embodiment the microorganism that is able to ferment at least one C5 sugar is a yeast. In an embodiment, the yeast belongs to the genus *Saccharomyces*, preferably of the species *Saccharomyces cerevisiae*. The yeast, e.g. *Saccharomyces cerevisiae*, used in the processes according to the present invention is capable of converting hexose (C6) sugars and pentose (C5) sugars. The yeast, e.g. *Saccharomyces cerevisiae*, used in the processes according to the present invention can anaerobically ferment at least one C6 sugar and at least one C5 sugar. For example, the yeast is capable of using L-arabinose and xylose in addition to glucose anaerobically. In an embodiment, the yeast is capable of converting L-arabinose into L-ribulose and/or xylulose 5-phosphate and/or into a desired fermentation product, for example into ethanol. Organisms, for example *Saccharomyces cerevisiae* strains, able to produce ethanol from L-arabinose may be produced by modifying a host yeast introducing the araA (L-arabinose isomerase), araB (L-ribuloglyoxalate) and araD (L-ribulose-5-P4-epimerase) genes from a suitable source. Such genes may be introduced into a host cell in order that it is capable of using arabinose. Such an approach is given is described in WO2003/095627. araA, araB and araD genes from *Lactobacillus plantarum* may be used and are disclosed in WO2008/041840. The araA gene from *Bacillus subtilis* and the araB and araD genes from *Escherichia coli* may be used and are disclosed in EP1499708. In another embodiment, araA, araB and araD genes may derived from of at least one of the genus *Clavibacter, Arthrobacter* and/or *Gramella*, in particular one of *Clavibacter michiganensis, Arthrobacter aurescens*, and/or *Gramella forsetii*, as disclosed in WO 2009011591. In an embodiment, the yeast may also comprise one or more copies of xylose isomerase gene and/or one or more copies of xylose reductase and/or xylitol dehydrogenase.

The yeast may comprise one or more genetic modifications to allow the yeast to ferment xylose. Examples of genetic modifications are introduction of one or more xy/A-gene, XYL1 gene and XYL2 gene and/or XKS1-gene; deletion of the aldose reductase (GRE3) gene; overexpression of PPP-genes TAL1, TKL1, RPE1 and RK/1 to allow the increase of the flux through the pentose phosphate pathway in the cell. Examples of genetically engineered yeast are described in EP1468093 and/or WO2006/009434.

An example of a suitable commercial yeast is RN1016 that is a xylose and glucose fermenting *Saccharomyces cerevisiae* strain from DSM, the Netherlands.

In an embodiment, the fermentation process for the production of ethanol is anaerobic. Anaerobic has already been defined earlier herein. In another preferred embodiment, the fermentation process for the production of ethanol is aerobic. In another preferred embodiment, the fermentation process for the production of ethanol is under oxygen-limited conditions, more preferably aerobic and under oxygen-limited conditions. Oxygen-limited conditions have already been defined earlier herein.

The volumetric ethanol productivity is preferably at least 0.5, 1.0, 1.5, 2.0, 2.5, 3.0, 5.0 or 10.0 g ethanol per litre per hour. The ethanol yield on L-arabinose and optionally xylose and/or glucose in the process preferably is at least 20, 25, 30, 35, 40, 45, 50, 60, 70, 80, 90, 95 or 98%. The ethanol yield is herein defined as a percentage of the theoretical maximum yield, which, for glucose and L-arabinose and optionally xylose is 0.51 g ethanol per g glucose or xylose.

Alternatively to the fermentation processes described above, at least two distinct cells may be used, this means this process is a co-fermentation process. All preferred embodiments of the fermentation processes as described above are also preferred embodiments of this co-fermentation process: identity of the fermentation product, identity of source of L-arabinose and source of xylose, conditions of fermentation (aerobic or anaerobic conditions, oxygen-limited conditions, temperature at which the process is being carried out, productivity of ethanol, yield of ethanol).

In another embodiment the fermenting microorganism is an organic acid producing microorganism. In an embodiment the fermentation is performed in one or more containers. The organic acid producing microorganisms may be a prokaryotic or eukaryotic organism. The microorganism used in the process may be a genetically engineered microorganism. Examples of suitable organic acid producing organisms are yeasts, for instance *Saccharomyces*, e.g. *Saccharomyces cerevisiae*; fungi for instance *Aspergillus* strains, such as *Aspergillus niger* and *Aspergillus fumigatus*, *Byssochlamys nivea*, *Lentinus degener*, *Paecilomyces varioti* and *Penicillium viniferum*; and bacteria, for instance *Anaerobiospirillum succiniciproducens*, *Actinobacillus succinogenes*, *Mannhei succiniciproducers* MBEL 55E, *Escherichia coli*, *Propionibacterium species*, *Pectinatus* sp., *Bacteroides* sp., such as *Bacteroides amylophilus*, *Ruminococcus flavefaciens*, *Prevotella ruminicola*, *Succcinimonas amylolytica*, *Succinivibrio dextrinisolvens*, *Wolinella succinogenes*, and *Cytophaga succinicans*. In an embodiment the organic acid producing microorganism that is able to ferment at least one C6 sugar is a yeast. In an embodiment, the yeast belongs to the genus *Saccharomyces*, preferably of the species *Saccharomyces cerevisiae*. The yeast, e.g. *Saccharomyces cerevisiae*, used in the production processes of organic acid according to the present invention is capable of converting hexose (C6) sugars. The yeast, e.g. *Saccharomyces cerevisiae*, used in the processes according to the present invention can anaerobically ferment at least one C6 sugar.

Fermentation products that may be produced by the process for producing a fermentation product from a cellulosic substrate according to the invention can be any substance derived from fermentation. They include, but are not limited to, alcohol (such as arabinitol, butanol, ethanol, glycerol, methanol, 1,3-propanediol, sorbitol, and xylitol); organic acid (such as acetic acid, acetonic acid, adipic acid, ascorbic acid, acrylic acid, citric acid, 2,5-diketo-D-gluconic acid, formic acid, fumaric acid, glucaric acid, gluconic acid, glucuronic acid, glutaric acid, 3-hydroxypropionic acid, itaconic acid, lactic acid, maleic acid, malic acid, malonic acid, oxalic acid, oxaloacetic acid, propionic acid, succinic acid, and xylonic acid); ketones (such as acetone); amino acids (such as aspartic acid, glutamic acid, glycine, lysine, serine, tryptophan, and threonine); alkanes (such as pentane, hexane, heptane, octane, nonane, decane, undecane, and dodecane), cycloalkanes (such as cyclopentane, cyclohexane, cycloheptane, and cyclooctane), alkenes (such as pentene, hexene, heptene, and octene); and gases (such as methane, hydrogen ($H_2$), carbon dioxide ($CO_2$), and carbon monoxide (CO)). The fermentation product can also be a protein, a vitamin, a pharmaceutical, an animal feed supplement, a specialty chemical, a chemical feedstock, a plastic, a solvent, ethylene, an enzyme. In a preferred embodiment the organic acid is succinic acid and/or the alcohol is ethanol.

The processes according to the invention may comprise recovery of all kinds of products made during the processes including fermentation products such as ethanol and succinic acid. A fermentation product may be separated from the fermentation broth in manner know to the skilled person. Examples of techniques for recovery include, but are not limited to, chromatography, electrophoretic procedures, differential solubility, distillation, or extraction. For each fermentation product, the skilled person will thus be able to select a proper separation technique. For instance, ethanol may be separated from a yeast fermentation broth by distillation, for instance steam distillation/vacuum distillation in conventional way.

The invention also pertains to the use of one inoculum bioreactor to supply fungal cells to at least two production bioreactors, preferably to the use of one inoculum bioreactor to supply fungal cells to two production bioreactors. All features and embodiments as described above do also apply for the use of one inoculum bioreactor to supply fungal cells to (at least) two production bioreactors. In an embodiment the inoculum bioreactor supplies fungal cells to two production bioreactors, three production bioreactors, four production bioreactors or even five production bioreactors.

The invention also pertains to a factory comprising one inoculum bioreactor that is coupled to at least two production bioreactors, preferably to a factory comprising one inoculum bioreactor that is coupled to two production bioreactors. All features and embodiments as described above do also apply for the factory comprising one inoculum bioreactor that is coupled to (at least) two production bioreactors. In an embodiment the inoculum bioreactor is coupled to two production bioreactors, three production bioreactors, four production bioreactors or even five production bioreactors.

EXAMPLES

Example 1

Enzyme Productivity Over CAPEX for a Plant Wherein Two Production Bioreactors are Inoculated by a Single Inoculum Train with a Ratio of the Gross Volumes of the Inoculum Bioreactor and the Production Bioreactor of 4.2%

A fermentative enzyme production plant has two production bioreactors that are operated in fed-batch mode and each have a gross volume of 120 $m^3$. Both production bioreactors are inoculated by a single inoculum train.

The first step of the inoculum train is a pre-culture of 0.8 kg, which is carried out as a batch process in a bioreactor with a gross volume of 2 l, and which is inoculated with 4*1 ml of a working cell bank of the production microorganism. The first pre-culture is used to inoculate a second pre-culture of 87 kg, which is carried out as a batch process in a bioreactor with a gross volume of 140 l. This second pre-culture serves to inoculate the inoculum bioreactor.

The inoculum cultivation is a batch process, carried out in an inoculum bioreactor with a gross volume of 5 $m^3$, containing 3 ton of broth after inoculation with the second pre-culture. The initial biomass concentration in the inoculum bioreactor is 0.15 g/kg dry matter. During exponential growth in a batch cultivation, the microorganism attains a maximum growth rate of 0.15 $h^{-1}$. At the end of the inoculum fermentation the biomass concentration has reached a value of 5 g/kg. This represents an increase of the biomass concentration during this stage by a factor 34.5. At the maximum growth rate, this requires 23.6 hours.

The duration of the production cultivations equals the duration of the batch phase plus 100 hours of feeding phase plus 24 hours turn around time at the end of fermentation. During the turn around time, the fermentor is emptied, cleaned, filled with fresh medium and sterilized. The production cultivation starts with 64 tons of batch medium. The batch phase serves to increase the biomass concentration in the production bioreactor from the initial concentration after inoculation to 6 g/kg dry matter.

Inoculation of the 64 ton of medium in the production cultivation with 3 ton of inoculum containing 5 g/kg biomass, gives an initial biomass concentration in the production cultivation of 0.22 g/kg dry matter. The batch phase duration needed to increase the biomass concentration to 6 g/kg is 21.9 hours. This leads to a total duration of the production cultivation of 146 hours.

Every 146 hours, the inoculum train needs to inoculate two production bioreactors. As stated before, the inoculum cultivation requires 23.6 hours. Taking into account a turn around time of 24 hours for the inoculum bioreactor, two inoculum cultivation cycles including turn around time can be easily finished within the duration of a production cultivation.

At the end of the main cultivation the weight of the fermentation broth has attained 80 ton and the concentration of the final product, an enzyme, is 1 U/g (or $1*10^6$ U/ton), where U is defined as an arbitrary amount of enzyme substrate converted by the enzyme per time unit. The productivity of the fermentation plant is defined as the amount of enzyme product produced per time. In this example, the plant produces 2 fermentors*80 ton*$1*10^6$ U/ton/146 h, which equals $1.10*10^6$ U/h.

In this example, the ratio of the gross volumes of the inoculum bioreactor and the production bioreactor is 5 m$^3$/120 m$^3$*100%=4.2%. The capital needed for a single production bioreactor of the plant is set at an arbitrary amount of X euros. During construction of the plant it was established that the capital needed for a bioreactor, including auxiliary equipment and installation, scales with the gross volume of the bioreactor to the power 0.5. Thus, the capital needed for the inoculum bioreactor can be calculated as X*(5 m$^3$/120 m$^3$)$^{0.5}$=0.20*X euros. The capital needed for the combined inoculum plus two production bioreactors of the plant therefore equalled 2*X+0.20*X=2.20*X euros.

The ratio of the enzyme productivity over the capital needed for the inoculum plus production bioreactors of this fermentation plant equals $1.10*10^6$ U/h/(2.20*X) euros=$0.50*10^6$/X U/h/euro.

Example 2

Enzyme Productivity Over CAPEX for a Plant Wherein Two Production Bioreactors are Inoculated by a Single Inoculum Train with a Ratio of the Gross Volumes of the Inoculum Bioreactor and the Production Bioreactor of 2%

A fermentative enzyme production plant has two production bioreactors that are operated in fed-batch mode and each have a gross volume of 120 m$^3$. Both production bioreactors are inoculated by a single inoculum train.

The first step of the inoculum train is a pre-culture of 0.4 kg, which is carried out as a batch process in a bioreactor with a gross volume of 1 l, and which is inoculated with 2*1 ml of a working cell bank of the production microorganism. The first pre-culture is used to inoculate a second pre-culture of 42 kg, which is carried out as a batch process in a bioreactor with a gross volume of 68 l. This second pre-culture serves to inoculate the inoculum bioreactor.

The inoculum cultivation is a batch process, carried out in an inoculum bioreactor with a gross volume of 2.4 m$^3$, containing 1.45 ton of broth after inoculation with the second pre-culture. The initial biomass concentration in the inoculum bioreactor is 0.15 g/kg dry matter. During exponential growth in a batch cultivation, the microorganism attains a maximum growth rate of 0.15 h$^{-1}$. At the end of the inoculum fermentation the biomass concentration has reached a value of 5 g/kg. This represents an increase of the biomass concentration during this stage by a factor 34.5. At the maximum growth rate, this requires 23.6 hours.

The duration of the production cultivations equals the duration of the batch phase plus 100 hours of feeding phase plus 24 hours turn around time at the end of fermentation. During the turn around time, the fermentor is emptied, cleaned, filled with fresh medium and sterilized. The production cultivation starts with 65.6 tons of batch medium. The batch phase serves to increase the biomass concentration in the production bioreactor from the initial concentration after inoculation to 6 g/kg dry matter.

Inoculation of the 65.6 ton of medium in the production cultivation with 1.45 ton of inoculum containing 5 g/kg biomass, gives an initial biomass concentration in the production cultivation of 0.11 g/kg dry matter. The batch phase duration needed to increase the biomass concentration to 6 g/kg is 26.8 hours. This leads to a total duration of the production cultivation of 151 hours.

Every 151 hours, the inoculum train needs to inoculate two production bioreactors. As stated before, the inoculum cultivation requires 23.6 hours. Taking into account a turn around time of 24 hours for the inoculum bioreactor, two inoculum cultivation cycles including turn around time can be easily finished within the duration of a production cultivation.

At the end of the main cultivation the weight of the fermentation broth has attained 80 ton and the concentration of the final product, an enzyme, is 1 U/g (or $1*10^6$ U/ton), where U is defined as an arbitrary amount of enzyme substrate converted by the enzyme per time unit. The productivity of the fermentation plant is defined as the amount of enzyme product produced per time. In this example, the plant produces 2 fermentors*80 ton*$1*10^6$ U/ton/151 h, which equals $1.06*10^6$ U/h.

In this example, the ratio of the gross volumes of the inoculum bioreactor and the production bioreactor is 2.4 m$^3$/120 m$^3$*100%=2.0%. The capital needed for a single production bioreactor of the plant is set at an arbitrary amount of X euros. During construction of the plant it was established that the capital needed for a bioreactor, including auxiliary equipment and installation, scales with the gross volume of the bioreactor to the power 0.5. Thus, the capital needed for the inoculum bioreactor can be calculated as X*(2.4 m$^3$/120 m$^3$)$^{0.5}$=0.14*X euros. The capital needed for the combined inoculum plus two production bioreactors of the plant therefore equalled 2*X+0.14*X=2.14*X euros.

The ratio of the enzyme productivity over the capital needed for the inoculum plus production bioreactors of this fermentation plant equals $1.06*10^6$ U/h/(2.14*X) euros=$0.50*10^6$/X U/h/euro. This ratio is 99.6% of the same ratio calculated in example 1.

Example 3

Enzyme Productivity Over CAPEX for a Plant Wherein Two Production Bioreactors are Inoculated by a Single Inoculum Train with a Ratio of the Gross Volumes of the Inoculum Bioreactor and the Production Bioreactor of 8%

A fermentative enzyme production plant has two production bioreactors that are operated in fed-batch mode and each have a gross volume of 120 m$^3$. Both production bioreactors are inoculated by a single inoculum train.

The first step of the inoculum train is a pre-culture of 1.6 kg, which is carried out as a batch process in a bioreactor with a gross volume of 4 l, and which is inoculated with 8*1 ml of a working cell bank of the production microorganism. The first pre-culture is used to inoculate a second pre-culture of 167 kg, which is carried out as a batch process in a bioreactor with a gross volume of 268 l. This second pre-culture serves to inoculate the inoculum bioreactor.

The inoculum cultivation is a batch process, carried out in an inoculum bioreactor with a gross volume of 9.6 m$^3$, containing 5.75 ton of broth after inoculation with the second pre-culture. The initial biomass concentration in the inoculum bioreactor is 0.15 g/kg dry matter. During exponential growth in a batch cultivation, the microorganism attains a maximum growth rate of 0.15 h$^{-1}$. At the end of the inoculum fermentation the biomass concentration has reached a value of 5 g/kg. This represents an increase of the biomass concentration during this stage by a factor 34.5. At the maximum growth rate, this requires 23.6 hours.

The duration of the production cultivations equals the duration of the batch phase plus 100 hours of feeding phase plus 24 hours turn around time at the end of fermentation. During the turn around time, the fermentor is emptied, cleaned, filled with fresh medium and sterilized. The production cultivation starts with 61.3 tons of batch medium. The batch phase serves to increase the biomass concentration in the production bioreactor from the initial concentration after inoculation to 6 g/kg dry matter.

Inoculation of the 61.3 ton of medium in the production cultivation with 5.75 ton of inoculum containing 5 g/kg biomass, gives an initial biomass concentration in the production cultivation of 0.43 g/kg dry matter. The batch phase duration needed to increase the biomass concentration to 6 g/kg is 17.6 hours. This leads to a total duration of the production cultivation of 142 hours.

Every 142 hours, the inoculum train needs to inoculate two production bioreactors. As stated before, the inoculum cultivation requires 23.6 hours. Taking into account a turn around time of 24 hours for the inoculum bioreactor, two inoculum cultivation cycles including turn around time can be easily finished within the duration of a production cultivation.

At the end of the main cultivation the weight of the fermentation broth has attained 80 ton and the concentration of the final product, an enzyme, is 1 U/g (or 1*10$^6$ U/ton), where U is defined as an arbitrary amount of enzyme substrate converted by the enzyme per time unit. The productivity of the fermentation plant is defined as the amount of enzyme product produced per time. In this example, the plant produces 2 fermentors*80 ton*1*10$^6$ U/ton/142 h, which equals 1.13*10$^6$ U/h.

In this example, the ratio of the gross volumes of the inoculum bioreactor and the production bioreactor is 9.6 m$^3$/120 m$^3$*100%=8.0%. The capital needed for a single production bioreactor of the plant is set at an arbitrary amount of X euros. During construction of the plant it was established that the capital needed for a bioreactor, including auxiliary equipment and installation, scales with the gross volume of the bioreactor to the power 0.5. Thus, the capital needed for the inoculum bioreactor can be calculated as X*(9.6 m$^3$/120 m$^3$)$^{0.5}$=0.28*X euros. The capital needed for the combined inoculum plus two production bioreactors of the plant therefore equalled 2*X+0.28*X=2.28*X euros.

The ratio of the enzyme productivity over the capital needed for the inoculum plus production bioreactors of this fermentation plant equals 1.13*10$^6$ U/h/(2.28*X) euros=0.50*10$^6$/X U/h/euro. This ratio is 99.5% of the same ratio calculated in example 1.

Example 4

Enzyme Productivity Over CAPEX for a Plant Wherein Two Production Bioreactors are Inoculated by a Single Inoculum Train with a Ratio of the Gross Volumes of the Inoculum Bioreactor and the Production Bioreactor of 0.5%

A fermentative enzyme production plant has two production bioreactors that are operated in fed-batch mode and each have a gross volume of 120 m$^3$. Both production bioreactors are inoculated by a single inoculum train.

The first step of the inoculum train is a pre-culture of 0.1 kg, which is carried out as a batch process in a bioreactor with a gross volume of 0.3 l, and which is inoculated with 0.5 ml of a working cell bank of the production microorganism. The first pre-culture is used to inoculate a second pre-culture of 10 kg, which is carried out as a batch process in a bioreactor with a gross volume of 15 l. This second pre-culture serves to inoculate the inoculum bioreactor.

The inoculum cultivation is a batch process, carried out in an inoculum bioreactor with a gross volume of 0.55 m$^3$, containing 330 kg of broth after inoculation with the second pre-culture. The initial biomass concentration in the inoculum bioreactor is 0.15 g/kg dry matter. During exponential growth in a batch cultivation, the microorganism attains a maximum growth rate of 0.15 h$^{-1}$. At the end of the inoculum fermentation the biomass concentration has reached a value of 5 g/kg. This represents an increase of the biomass concentration during this stage by a factor 34.5. At the maximum growth rate, this requires 23.6 hours.

The duration of the production cultivations equals the duration of the batch phase plus 100 hours of feeding phase plus 24 hours turn around time at the end of fermentation. During the turn around time, the fermentor is emptied, cleaned, filled with fresh medium and sterilized. The production cultivation starts with 66.7 tons of batch medium. The batch phase serves to increase the biomass concentration in the production bioreactor from the initial concentration after inoculation to 6 g/kg dry matter.

Inoculation of the 66.7 ton of medium in the production cultivation with 330 kg of inoculum containing 5 g/kg biomass, gives an initial biomass concentration in the production cultivation of 0.025 g/kg dry matter. The batch phase duration needed to increase the biomass concentration to 6 g/kg is 36.6 hours. This leads to a total duration of the production cultivation of 161 hours.

Every 161 hours, the inoculum train needs to inoculate two production bioreactors. As stated before, the inoculum cultivation requires 23.6 hours. Taking into account a turn around time of 24 hours for the inoculum bioreactor, two inoculum cultivation cycles including turn around time can be easily finished within the duration of a production cultivation.

At the end of the main cultivation the weight of the fermentation broth has attained 80 ton and the concentration of the final product, an enzyme, is 1 U/g (or 1*10$^6$ U/ton), where U is defined as an arbitrary amount of enzyme substrate converted by the enzyme per time unit. The productivity of the fermentation plant is defined as the amount of enzyme product produced per time. In this example, the plant produces 2 fermentors*80 ton*1*10$^6$ U/ton/161 h, which equals 1.00*10$^6$ U/h.

In this example, the ratio of the gross volumes of the inoculum bioreactor and the production bioreactor is 0.55 m$^3$/120 m$^3$*100%=0.5%. The capital needed for a single production bioreactor of the plant is set at an arbitrary amount of X euros. During construction of the plant it was established that the capital needed for a bioreactor, including auxiliary equipment and installation, scales with the gross volume of the bioreactor to the power 0.5. Thus, the capital needed for the inoculum bioreactor can be calculated as X*(0.55 m$^3$/120 m$^3$)$^{0.5}$=0.07*X euros. The capital needed for the combined inoculum plus two production bioreactors of the plant therefore equalled 2*X+0.07*X=2.07*X euros.

The ratio of the enzyme productivity over the capital needed for the inoculum plus production bioreactors of this fermentation plant equals $1.00*10^6$ U/h/(2.07*X) euros=$0.48*10^6$/X U/h/euro. This ratio is 96.8% of the same ratio calculated in example 1.

Example 5

Enzyme Productivity Over CAPEX for a Plant Wherein Two Production Bioreactors are Inoculated by a Single Inoculum Train with a Ratio of the Gross Volumes of the Inoculum Bioreactor and the Production Bioreactor of 20%.

A fermentative enzyme production plant has two production bioreactors that are operated in fed-batch mode and each have a gross volume of 120 m$^3$. Both production bioreactors are inoculated by a single inoculum train.

The first step of the inoculum train is a pre-culture of 3.8 kg, which is carried out as a batch process in a bioreactor with a gross volume of 8 l, and which is inoculated with 19*1 ml of a working cell bank of the production microorganism. The first pre-culture is used to inoculate a second pre-culture of 418 kg, which is carried out as a batch process in a bioreactor with a gross volume of 672 l. This second pre-culture serves to inoculate the inoculum bioreactor.

The inoculum cultivation is a batch process, carried out in an inoculum bioreactor with a gross volume of 24 m$^3$, containing 14.4 ton of broth after inoculation with the second pre-culture. The initial biomass concentration in the inoculum bioreactor is 0.15 g/kg dry matter. During exponential growth in a batch cultivation, the microorganism attains a maximum growth rate of 0.15 h$^{-1}$. At the end of the inoculum fermentation the biomass concentration has reached a value of 5 g/kg. This represents an increase of the biomass concentration during this stage by a factor 34.5. At the maximum growth rate, this requires 23.6 hours.

The duration of the production cultivations equals the duration of the batch phase plus 100 hours of feeding phase plus 24 hours turn around time at the end of fermentation. During the turn around time, the fermentor is emptied, cleaned, filled with fresh medium and sterilized. The production cultivation starts with 52.6 tons of batch medium. The batch phase serves to increase the biomass concentration in the production bioreactor from the initial concentration after inoculation to 6 g/kg dry matter.

Inoculation of the 52.6 ton of medium in the production cultivation with 14.4 ton of inoculum containing 5 g/kg biomass, gives an initial biomass concentration in the production cultivation of 1.07 g/kg dry matter. The batch phase duration needed to increase the biomass concentration to 6 g/kg is 11.5 hours. This leads to a total duration of the production cultivation of 135 hours.

Every 135 hours, the inoculum train needs to inoculate two production bioreactors. As stated before, the inoculum cultivation requires 23.6 hours. Taking into account a turn around time of 24 hours for the inoculum bioreactor, two inoculum cultivation cycles including turn around time can be easily finished within the duration of a production cultivation.

At the end of the main cultivation the weight of the fermentation broth has attained 80 ton and the concentration of the final product, an enzyme, is 1 U/g (or $1*10^6$ U/ton), where U is defined as an arbitrary amount of enzyme substrate converted by the enzyme per time unit. The productivity of the fermentation plant is defined as the amount of enzyme product produced per time. In this example, the plant produces 2 fermentors*80 ton*$1*10^6$ U/ton/136 h, which equals $1.18*10^6$ U/h.

In this example, the ratio of the gross volumes of the inoculum bioreactor and the production bioreactor is 24 m$^3$/120 m$^3$*100%=20%. The capital needed for a single production bioreactor of the plant is set at an arbitrary amount of X euros. During construction of the plant it was established that the capital needed for a bioreactor, including auxiliary equipment and installation, scales with the gross volume of the bioreactor to the power 0.5. Thus, the capital needed for the inoculum bioreactor can be calculated as X*(24 m$^3$/120 m$^3$)$^{0.5}$=0.45*X euros. The capital needed for the combined inoculum plus two production bioreactors of the plant therefore equalled 2*X+0.45*X=2.45*X euros.

The ratio of the enzyme productivity over the capital needed for the inoculum plus production bioreactors of this fermentation plant equals $1.18*10^6$ U/h/(2.45*X) euros=$0.48*10^6$/X U/h/euro. This ratio is 97.0% of the same ratio calculated in example 1.

Example 6

Enzyme Productivity Over CAPEX for a Plant Wherein Two Production Bioreactors are Inoculated by Two Inoculum Trains with a Ratio of the Gross Volumes of the Inoculum Bioreactor and the Production Bioreactor of 4.2%

A fermentative enzyme production plant has two production bioreactors that are operated in fed-batch mode and each have a gross volume of 120 m$^3$. The production bioreactors are inoculated by two inoculum trains.

The first step of each inoculum train is a pre-culture of 0.8 kg, which is carried out as a batch process in a bioreactor with a gross volume of 2 l, and which is inoculated with 41 ml of a working cell bank of the production microorganism. The first pre-culture is used to inoculate a second pre-culture of 87 kg, which is carried out as a batch process in a bioreactor with a gross volume of 140 l. This second pre-culture serves to inoculate the inoculum bioreactor.

The inoculum cultivation is a batch process, carried out in an inoculum bioreactor with a gross volume of 5 m$^3$, containing 3 ton of broth after inoculation with the second pre-culture. The initial biomass concentration in the inoculum bioreactor is 0.15 g/kg dry matter. During exponential growth in a batch cultivation, the microorganism attains a maximum growth rate of 0.15 h$^{-1}$. At the end of the inoculum fermentation the biomass concentration has reached a value of 5 g/kg. This represents an increase of the biomass concentration during this stage by a factor 34.5. At the maximum growth rate, this requires 23.6 hours.

The duration of the production cultivations equals the duration of the batch phase plus 100 hours of feeding phase plus 24 hours turn around time at the end of fermentation. During the turn around time, the fermentor is emptied, cleaned, filled with fresh medium and sterilized. The production cultivation starts with 64 tons of batch medium. The batch phase serves to increase the biomass concentration in the production bioreactor from the initial concentration after inoculation to 6 g/kg dry matter.

Inoculation of the 64 ton of medium in the production cultivation with 3 ton of inoculum containing 5 g/kg biomass, gives an initial biomass concentration in the production cultivation of 0.22 g/kg dry matter. The batch phase duration needed to increase the biomass concentration to 6 g/kg is 21.9 hours. This leads to a total duration of the production cultivation of 146 hours.

Every 146 hours, the inoculum train needs to inoculate a single production bioreactor. As stated before, the inoculum cultivation requires 23.6 hours. Taking into account a turn around time of 24 hours for the inoculum bioreactor, one inoculum cultivation cycle including turn around time can be easily finished within the duration of a production cultivation. In fact, each inoculum train is idle most of the time.

At the end of the main cultivation the weight of the fermentation broth has attained 80 ton and the concentration of the final product, an enzyme, is 1 U/g (or $1*10^6$ U/ton), where U is defined as an arbitrary amount of enzyme substrate converted by the enzyme per time unit. The productivity of the fermentation plant is defined as the amount of enzyme product produced per time. In this example, the plant produces 2 fermentors*80 ton*$1*10^6$ U/ton/146 h, which equals $1.10*10^6$ U/h.

In this example, the ratio of the gross volumes of the inoculum bioreactor and the production bioreactor is 5 m³/120 m³*100%=4.2%. The capital needed for a single production bioreactor of the plant is set at an arbitrary amount of X euros. During construction of the plant it was established that the capital needed for a bioreactor, including auxiliary equipment and installation, scales with the gross volume of the bioreactor to the power 0.5. Thus, the capital needed for the inoculum bioreactor can be calculated as $X*(5\ m^3/120\ m^3)^{0.5}=0.20*X$ euros. The capital needed for the combined two inoculum plus two production bioreactors of the plant therefore equalled $2*X+2*0.20*X=2.41*X$ euros.

The ratio of the enzyme productivity over the capital needed for the inoculum plus production bioreactors of this fermentation plant equals $1.10*10^6$ U/h/(2.41*X) euros=$0.46*10^6$/X U/h/euro. This ratio is 91.5% of the same ratio calculated in example 1.

The invention claimed is:

1. A process for producing an enzyme or an enzyme composition, the process comprising:
    a) preparing a fungal inoculum comprising fungal cells in an inoculum bioreactor,
    b) transferring the inoculum to a first of two or more production bioreactors, said first production bioreactor being ready for inoculation,
    c) culturing the fungal cells in the first production bioreactor to produce the enzyme or enzyme composition,
    d) emptying a second of the two or more production bioreactors, said second production bioreactor having reached the end of fermentation, and preparing the second production bioreactor for a new production fermentation,
    e) after (b), but before completion of (d), preparing a second fungal inoculum comprising fungal cells in the inoculum bioreactor,
    f) transferring the second inoculum to the second of the two or more production bioreactors, said second production bioreactor being ready for inoculation,
    g) culturing the fungal cells in the second production bioreactor to produce the enzyme or enzyme composition,
    h) emptying the first of the two or more production bioreactors, said first production bioreactor having reached the end of fermentation, and preparing the first production bioreactor for a new production fermentation, and
    i) after (f), but before completion of (h), repeating at least (a), and after completion of (h) repeating at least (b)-(e),
    wherein the first and/or second production bioreactors have a gross vessel volume of 20,000 l to 300,000 l, the inoculum bioreactor has a gross vessel volume of 300 l to 15,000 l and the ratio of the gross vessel volume of the inoculum bioreactor to the gross vessel volume of the first production bioreactor is from 2% to 4.5%, and/or the ratio of the gross vessel volume of the inoculum bioreactor to the gross vessel volume of the second production bioreactor is from 2% to 4.5%.

2. A process for producing an enzyme or an enzyme composition, the process comprising:
    a) preparing a fungal inoculum comprising fungal cells in an inoculum bioreactor,
    b) transferring the inoculum to a first of three or more production bioreactors, said first production bioreactor being ready for inoculation,
    c) culturing the fungal cells in the first production bioreactor to produce the enzyme or enzyme composition,
    d) emptying a second of the three or more production bioreactors, said second production bioreactor having reached the end of fermentation, and preparing the second production bioreactor for a new production fermentation,
    e) after (b), but before completion of (d), preparing a second fungal inoculum comprising fungal cells in the inoculum bioreactor,
    f) transferring the second inoculum to the second of the three or more production bioreactors, said second production bioreactor being ready for inoculation,
    g) culturing the fungal cells in the second production bioreactor to produce the enzyme or enzyme composition,
    h) emptying a third of the three or more production bioreactors, said third production bioreactor having reached the end of fermentation, and preparing the third production bioreactor for a new production fermentation,
    i) after (f), but before completion of (h), preparing a third fungal inoculum comprising fungal cells in the inoculum bioreactor,
    j) transferring the third inoculum to the third of the three or more production bioreactors, said third production bioreactor being ready for inoculation,
    k) culturing the fungal cells in the third production bioreactor to produce the enzyme or enzyme composition,
    l) emptying the first of the three or more production bioreactors, said first production bioreactor having reached the end of fermentation, and preparing the first production bioreactor for a new production fermentation, and
    m) after (j), but before completion of (l), repeating at least (a), and after completion of (h) repeating at least (b)-(e),
    wherein the first, second and/or third production bioreactor have a gross vessel volume of 20,000 l to 300,000 l, the inoculum bioreactor has a gross vessel volume of 300 l to 15,000 l and the ratio of the gross vessel volume of the inoculum bioreactor to the gross vessel volume of the first production bioreactor is from 2% to 4.5%, and/or the ratio of the gross vessel volume of the inoculum bioreactor to the gross vessel volume of the second production bioreactor is from 2% to 4.5%, and/or the ratio of the gross vessel volume of the inoculum bioreactor to the gross vessel volume of the third production bioreactor is from 2% to 4.5%.

3. The process according to claim 1, wherein the enzyme or enzyme composition produced in (c) and (g) are the same.

4. The process according to claim 1, wherein the fungus is a filamentous fungus.

5. The process according to claim 1, wherein the first and second production bioreactors have an identical gross vessel volume.

6. The process according to claim 1, wherein
(a) and/or (e) and/or (i) are done in a batch mode, and/or
(c) and/or (g) are done in a fed-batch mode.

7. The process according to claim 1, further comprising storing the enzyme or enzyme composition produced in (c) and/or (g) in a storage tank.

8. The process according to claim 1, wherein (a) and/or (e) and/or (i) are done for 1 to 60 hours, and/or wherein (c) and/or (g) are done for 10 to 300 hours.

9. A process for degrading a cellulosic substrate, the process comprising:
   a) performing the process according to claim 1, and
   b) adding the enzyme or enzyme composition produced in (c) and/or (g) to the cellulosic substrate to degrade the cellulosic substrate.

10. A process for producing a fermentation product from a cellulosic substrate, the process comprising:
   a) performing the process according to claim 1,
   b) adding the enzyme or enzyme composition produced in (c) and/or (g) to the cellulosic substrate to degrade the cellulosic substrate, and
   c) fermenting the degraded cellulosic substrate by a fermenting microorganism to obtain the fermentation product.

11. The process according to claim 2, wherein
the enzyme or enzyme composition produced in (c), (g) and (k) are the same.

12. The process according to claim 2, wherein the fungus is a filamentous fungus.

13. The process according to claim 2, wherein the first, second and/or third production bioreactors have an identical gross vessel volume.

14. The process according to claim 2, wherein
(a) and/or (e) and/or (i) are done in a batch mode, and/or
(c) and/or (g) and/or (k) are done in a fed-batch mode.

15. The process according to claim 2, further comprising storing the enzyme or enzyme composition produced in (c) and/or (g) and/or (k) in a storage tank.

16. The process according to claim 2, wherein (a) and/or (e) and/or (i) are done for 1 to 60 hours, and/or wherein (c) and/or (g) and/or (k) are done for 10 to 300 hours.

17. A process for degrading a cellulosic substrate, the process comprising:
   a) performing the process according to claim 2, and
   b) adding the enzyme or enzyme composition produced in (c) and/or (g) and/or (k) to the cellulosic substrate to degrade the cellulosic substrate.

18. A process for producing a fermentation product from a cellulosic substrate, the process comprising:
   a) performing the process according to claim 2,
   b) adding the enzyme or enzyme composition produced in (c) and/or (g) and/or (k) to the cellulosic substrate to degrade the cellulosic substrate, and
   c) fermenting the degraded cellulosic substrate by a fermenting microorganism to obtain the fermentation product.

* * * * *